(12) United States Patent
Kasi et al.

(10) Patent No.: US 11,173,173 B2
(45) Date of Patent: Nov. 16, 2021

(54) METHODS FOR TREATING CHEMORESISTANT CANCER-INITIATING CELLS

(71) Applicants: UNIVERSITY OF CONNECTICUT, Farmington, CT (US); STOWERS INSTITUTE FOR MEDICAL RESEARCH, Kansas City, MO (US); UNIVERSITY OF KANSAS, Lawrence, KS (US)

(72) Inventors: Rajeswari Kasi, Windsor, CT (US); Linheng Li, Kansas City, MO (US); Xiuling Lu, Storrs, CT (US); John M. Perry, Kansas City, MO (US); Gurusingham Sitta Sittampalam, Fishers, IN (US); Anuradha Roy, Kansas City, MO (US); Xi C. He, Kansas City, MO (US)

(73) Assignees: UNIVERSITY OF CONNECTICUT, Farmington, CT (US); UNIVERSITY OF KANSAS, Lawrence, KS (US); STOWERS INSTITUTE FOR MEDICAL RESEARCH, Kansas City, MO (US)

( * ) Notice: Subject to any disclaimer, the term of this patent is extended or adjusted under 35 U.S.C. 154(b) by 176 days.

(21) Appl. No.: 15/745,875

(22) PCT Filed: Jul. 28, 2016

(86) PCT No.: PCT/US2016/044584
§ 371 (c)(1),
(2) Date: Jan. 18, 2018

(87) PCT Pub. No.: WO2017/019914
PCT Pub. Date: Feb. 2, 2017

(65) Prior Publication Data
US 2018/0207184 A1    Jul. 26, 2018

Related U.S. Application Data

(60) Provisional application No. 62/198,670, filed on Jul. 29, 2015.

(51) Int. Cl.
| | | |
|---|---|---|
| A61K 9/51 | (2006.01) |
| A61K 31/704 | (2006.01) |
| A61K 31/513 | (2006.01) |
| A61K 31/136 | (2006.01) |
| A61K 31/4745 | (2006.01) |
| A61K 45/06 | (2006.01) |
| A61K 31/573 | (2006.01) |
| A61K 9/00 | (2006.01) |
| A61K 31/18 | (2006.01) |
| A61K 31/475 | (2006.01) |
| A61K 31/519 | (2006.01) |
| A61K 31/7076 | (2006.01) |
| A61K 31/708 | (2006.01) |
| A61K 31/337 | (2006.01) |
| A61K 33/242 | (2019.01) |
| A61K 33/243 | (2019.01) |
| A61P 35/02 | (2006.01) |

(52) U.S. Cl.
CPC .......... *A61K 31/704* (2013.01); *A61K 9/0019* (2013.01); *A61K 9/5138* (2013.01); *A61K 9/5146* (2013.01); *A61K 31/136* (2013.01); *A61K 31/18* (2013.01); *A61K 31/337* (2013.01); *A61K 31/475* (2013.01); *A61K 31/4745* (2013.01); *A61K 31/513* (2013.01); *A61K 31/519* (2013.01); *A61K 31/573* (2013.01); *A61K 31/708* (2013.01); *A61K 31/7076* (2013.01); *A61K 33/242* (2019.01); *A61K 33/243* (2019.01); *A61K 45/06* (2013.01); *A61P 35/02* (2018.01); *A61K 9/0009* (2013.01)

(58) Field of Classification Search
None
See application file for complete search history.

(56) References Cited

U.S. PATENT DOCUMENTS

2012/0272346 A1* 10/2012 Stillman ............ A01K 67/0271
800/10

FOREIGN PATENT DOCUMENTS

| WO | 2015/054269 A1 | 4/2015 |
| WO | 2016/061135 A1 | 4/2016 |
| WO | 2016/061310 A2 | 4/2016 |

OTHER PUBLICATIONS

The International Search Report (ISR) with Written Opinion for PCT/US2016/044584 dated Sep. 14, 2016, pp. 1-16.
Yallapu, Murali M. et al. "Curcumin induces chemo/radio-sensitization in ovarian cancer cells and curcumin nanoparticles inhibit ovarian cancer cell growth" Journal of Ovarian Research (2010) vol. 3(11), pp. 1-12.
Nishida, Yoshihiro et al. "Low-dose chemotherapy with methotrexate and vinblastine for patients with desmoid tumors: relationship to CTNNB1 mutation status" Int J Clin Oncol (2015) vol. 20, pp. 1211-1217.
Nguyen, Chi Thanh et al. "Redox-sensitive nanoparticles from amphiphilic cholesterol-based block copolynlers for enhanced tumor intracellular release of doxorubicin" Naomedicine Nanotechnology, Biology, and Medicine (2015) vol. 11, pp. 2071-2082.

(Continued)

*Primary Examiner* — Jessica Worsham
(74) *Attorney, Agent, or Firm* — McDonnell Boehnen Hulbert & Berghoff LLP

(57) ABSTRACT

The disclosure provides methods of treating cancer by selectively inhibiting p-$S^{552}$-β-catenin, p-$T^{217}$-β-catenin, p-$T^{332}$-β-catenin, and/or p-$S^{675}$-β-catenin production and/or activity. Such methods also and/or limit cancer-initiating cells.

12 Claims, 11 Drawing Sheets

(56) References Cited

OTHER PUBLICATIONS

Gonzalez-Fajardo, Laura et al. "Reduced in vivo toxicity of doxorubicin by encapsulation in cholesterol-containing self-assembled nanoparticles" Pharmacological Research (2016) vol. 107, pp. 93-101.

Nguyen, Chi Thanh et al. "Self-assembled nanoparticles from thiol functionalized liquid crystalline brush block copolymers for dual encapsulation of doxorubicin and gold nanoparticles" Polymer Chemistry (2014) vol. 5, pp. 2774-2783.

* cited by examiner

US 11,173,173 B2

METHODS FOR TREATING CHEMORESISTANT CANCER-INITIATING CELLS

CROSS-REFERENCE TO RELATED APPLICATIONS

This application is a U.S. national phase of International Application No. PCT/US2016/044584, filed on Jul. 28, 2016, which claims priority to U.S. Provisional Application No. 62/198,670, filed Jul. 29, 2015, both of which are incorporated by reference herein in their entirety.

BACKGROUND OF THE INVENTION

Field of the Invention

The disclosure provides methods of treating cancer by selectively inhibiting p-$S^{552}$-β-catenin, p-$T^{217}$-β-catenin, p-$T^{332}$-β-catenin, and/or p-$S^{675}$-β-catenin production and/or activity. Such methods also reduce and/or limit cancer-initiating cells.

Description of Related Art

The cancer stem cell (CSC) model proposes that tumors are maintained by a unique sub-population of cells with self-renewal capacity that differentiate into mostly non-tumorigenic progeny. Some evidence suggests these often rare CSCs preferentially survive standard chemotherapeutic treatments, but distinguishing CSCs from the bulk of the tumor and specifically targeting them remains a considerable challenge. The recent renaissance in understanding the role of clonal evolution in tumorigenesis illuminated the challenge of acquired resistance and has led to two major models of tumorigenesis—the cancer stem cell and clonal evolution. These are not necessarily mutually exclusive and can be complementary. Both indicate that the main obstacle to durable cures is cancer heterogeneity. However, existing anti-cancer therapy largely fails to account for either model. Recent advances in targeted therapy are promising, but since cancer heterogeneity and evolution present multiple, moving targets, development of resistance is common. Unfortunately, little progress has been made in targeting the chemoresistant cells responsible for relapse. However, regardless of whether clonal evolution, cancer stem cell, or a hybrid model best explains therapeutic resistance, it has been noted that stemness may represent a critical target. Stemness refers to the molecular programs that govern and maintain the stem cell state, and central to this state is the ability to self-renew. Absent self-renewal, cancers cannot persist or regenerate following chemotherapy, but understanding and then targeting self-renewal remains an unmet challenge.

The link between tumorigenesis and aberrant self-renewal is illustrated by the Wnt/β-catenin and PI3K/Akt signaling pathways. Wnt signaling plays a prominent but complicated role in these processes. Several studies demonstrate a critical role for β-catenin in CSCs and indicate that CSCs can be targeted through β-catenin pathway inhibition, but suggest that this alone is not sufficient for eliminating tumors. The PI3K/Akt pathway, which is negatively regulated by the tumor-suppressor PTEN, is frequently dysregulated in cancer due to its central role in cell proliferation, growth, survival, and metabolism as well as stem cell regulation. Extensive efforts have focused on pharmacologically inhibiting this pathway for anti-cancer therapy. Nonetheless, emerging clinical data have shown only limited efficacy for PI3K pathway inhibitors, and animal studies showed that PI3K inhibitor treatment could lead to the outgrowth of resistant clones. Indeed, using a Pten mutant T-cell acute lymphocytic leukemia (T-ALL) mouse model, it was shown that rare, self-renewing chemoresistant leukemic stem cells (LSCs) identified as lineage negative (Lin$^-$) CD3$^+$c-Kit$^{Mid}$ cells and their bulk blast cell progeny had differential sensitivity to different targeted treatments. The Wnt/β-catenin and PI3K/Akt pathways have even been shown to cooperate in tumorigenesis. Pten deletion results in intestinal polyposis caused by excessive intestinal stem cell activity. Mechanistically, this effect is driven in part by Akt phosphorylation of β-catenin at serine 552 (p$S^{552}$-β-catenin), leading to β-catenin activation. Indeed, β-catenin was shown to confer resistance to PI3K and Akt inhibitors and promote metastasis in colon cancer. The tankyrase inhibitor XAV-939, an indirect inhibitor of β-catenin, was shown to reverse this resistance in vitro. Unfortunately, low activity of this inhibitor in vivo precludes effective clinical use.

SUMMARY OF INVENTION

Targeting the Wnt/β-catenin and PI3K/Akt pathways for more effective anti-cancer activity offers the potential but also the limitations as noted above. The inventors have found that that the Wnt/β-catenin and PI3K/Akt pathways cooperatively interact to promote HSC self-renewal and expansion. While activation of either pathway individually was not compatible with long-term self-renewal—with Pten deletion resulting in HSC proliferation but exhaustion due to excessive differentiation and β-catenin activation blocking differentiation but resulting in apoptosis of HSCs—in combination, the two cooperatively drove self-renewal and HSC expansion by blocking differentiation and apoptosis in proliferating HSCs (Perry, J. M. et al. Cooperation between both Wnt/β-catenin and PTEN/PI3K/Akt signaling promotes primitive hematopoietic stem cell self-renewal and expansion. Genes Dev 25, 1928-1942 (2011), incorporated by reference). Pharmacological agents stimulating both pathways in genetically normal HSCs led to expansion of untransformed stem cells; however, permanent, genetic activation of both pathways resulted in leukemic transformation.

Multiple lines of evidence indicate that self-renewing CSCs/LSCs are responsible for chemoresistance. Because the Wnt/β-catenin and PI3K/Akt pathways interact to stimulate self-renewal and through phosphorylation of β-catenin by Akt (p$S^{552}$-β-catenin), targeting p$S^{552}$-β-catenin may inhibit oncogenic self-renewal. In the methods of the disclosure, the normal self-renewal was stimulated to discover an inhibitor of oncogenic self-renewal.

Thus, in broad aspect, the invention provides methods of treating cancer, comprising administering to a subject in need thereof a pharmaceutically active molecule that is capable of selectively inhibiting p-$S^{552}$-β-catenin, p-$T^{217}$-β-catenin, p-$T^{332}$-β-catenin, and/or p-$S^{675}$-β-catenin production and/or activity, wherein the pharmaceutically active molecule is administered in an amount effective to reduce and/or limit cancer-initiating cells.

Surprisingly, the inventors found that doxorubicin (DXR, or Doxo, or DOX), a long-used chemotherapeutic agent, selectively inhibits p$S^{552}$-β-catenin with minimal effect on total β-catenin. At high doses typically used in the clinic, DXR acts as a DNA-damaging agent by inhibiting topoisomerase II. DXR and other chemotherapeutics preferentially target tumors, and DXR has such broad and efficacious anti-cancer activity relative to other chemotherapeutics. The inventors found that, by using low, metronomic doses of DXR, particularly through slow-release, long-circulating DXR nanoparticles (NanoDXR or NanoDoxo), leukemia-initiating activity of LSCs can be inhibited while sparing HSPCs. In vivo, this treatment reduced pS$^{552}$-β-catenin levels in LSCs, prevented LSC expansion, essentially eliminated LSC tumorigenic activity, and was accompanied by recovery of hematopoietic stem/progenitor cells (HSPCs, Lin$^-$Sca1$^+$c-Kit$^+$) and substantially increased survival. The inventors also found a dynamic relationship between rare LSCs and their bulk leukemic blast cell progeny in response to cytotoxic chemotherapy. Notably, it was found that binary targeting of bulk leukemic blasts with cytotoxic chemotherapy and chemoresistant LSCs by targeting pS$^{552}$-β-catenin-dependent oncogenic self-renewal is necessary for optimal survival. In distinguishing the unique properties of LSCs and their progeny, the inventors found that both populations must be differentially targeted at both the 'root' and 'branch' of cancer.

populations in control, single and double mutant thymus at 8-9 wpi. Representative FACS plots of control (upper panel) and double mutant (lower panel) thymus is shown in e. g-h, Double and single positive thymocyte populations from control, single and double mutants. Representative FACS plots of control (left panel) and double mutant (right panel) thymus is shown in g. Results are graphed as mean±SD.

Figure 7:
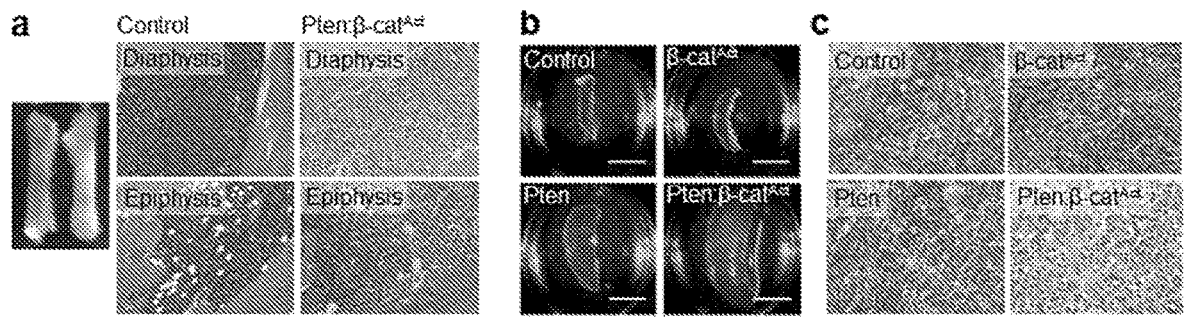

FIG. 7 illustrates Bone Marrow and spleen histology of Pten:β-catAct leukemic mice. a, Femur of control (left) and Pten:β-catAct mutants (right). H&E sections of bone marrow diaphysis and trabecular bone region of epiphysis. b, Representative spleens from control, single and double mutants. 1 cm scale bar. c, Masson's Trichrome stained sections of spleens from b.

Figure 8:
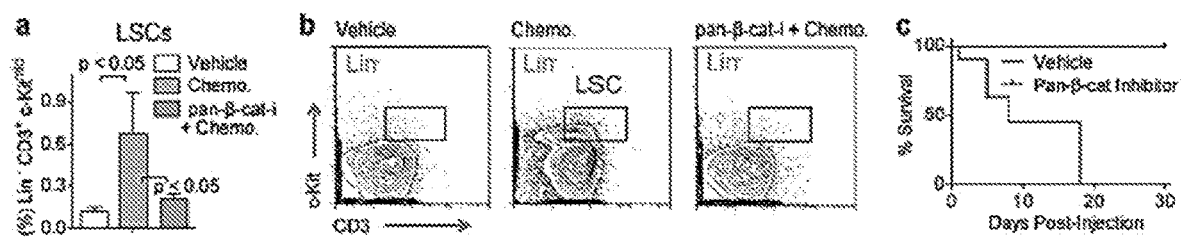

FIG. 8 illustrates inhibition of β-catenin prevents expansion of LSCs in response to chemotherapy but increases morbidity. a-b, Double mutant mice were treated with chemotherapy (Nelarabine+dexamethasone) with or without pan-β-catenin inhibitor. Flow cytometric analysis revealed that chemotherapy stimulated the expansion of LSCs. Additional treatment with pan-β-catenin inhibitor prevented this expansion; however, β-catenin's critical role in normal cellular function results in poor survival (c).

Figure 9:
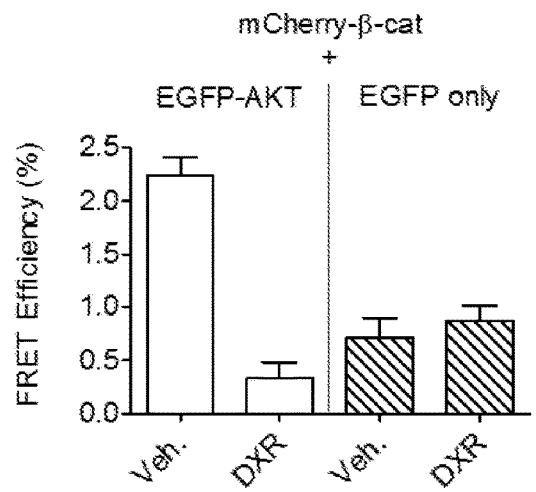

FIG. 9 shows FRET verification between Akt and β-catenin. While FRET was observed in mCherry-β-catenin+EGFP-AKT transfected cells and could be inhibited by DXR, essentially no discernible FRET occurred when mCherry-β-catenin was transfected with EGFP alone (see also FIG. 2e-f).

Figure 1:
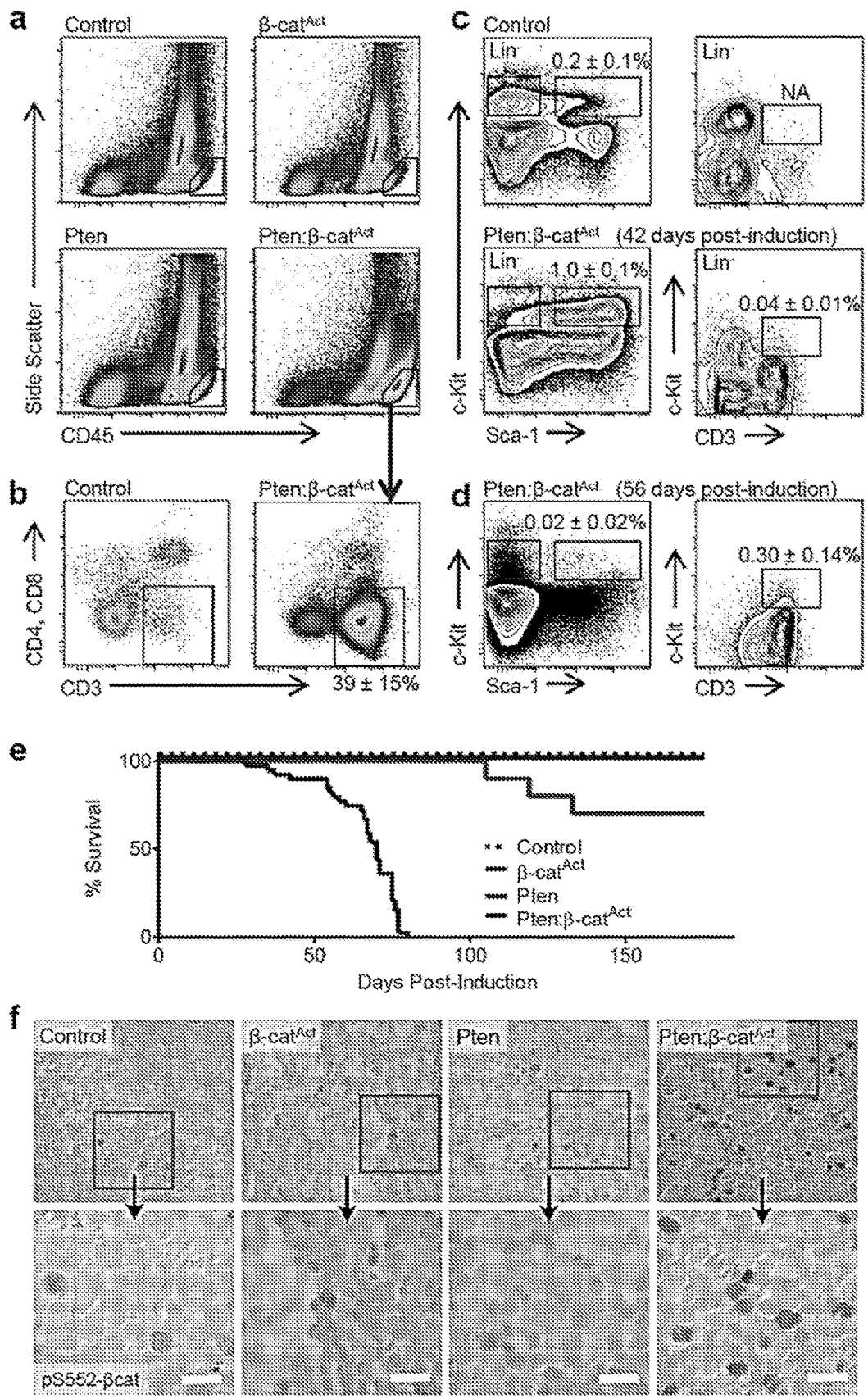
FIG. 1 illustrates that cooperative activation of the Wnt/β-catenin and PI3K/Akt pathways successively expands HSPCs, LSCs and T-ALL blast cells. Pten:β-cat$^{Act}$ mice were induced by tamoxifen. a, At 9 wpi, flow cytometry analysis of BM showed that all double mutants, but not single mutants, developed leukemia characterized by ≥20% CD45$^{Hi}$ blast crisis cells. b, These cells predominantly expressed CD3 but lacked both CD4 and CD8 expression, indicative of an early T-ALL. c, Prior to T-ALL development, Pten:β-cat$^{Act}$ mice exhibited expansion of HSPCs identified by flow cytometry as Lin$^-$Sca-1$^+$c-Kit$^+$ (LSK) cells. d, The HSPC population collapsed as LSCs, identified as Lin$^-$c-Kit$^{Mid}$ CD3$^+$ cells, expanded. e, Kaplan-Meier survival curves indicated that all double mutants, but not single mutants, succumbed to leukemia by 12 wpi. f, Anti-pS$^{552}$-β-catenin antibody staining (dark gray) of control, single and double mutant spleens counterstained with light H&E at 8 wpi. Frequencies are based on percent of total nucleated cells±standard deviation (SD). Scale bars, 10 μm.
Figure 10:
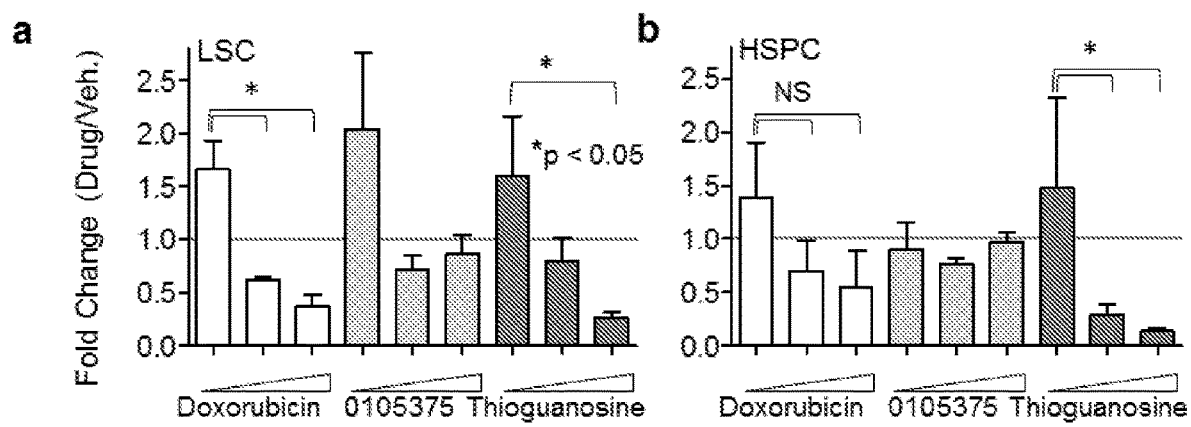

FIG. 10 illustrates that DXR preferentially inhibits LSC expansion in vitro. a-b, BM isolated from leukemic Pten:β-catAct mice at 8 wpi was cultured in HSC expansion media. Doxorubicin, 0105375, and thioguanosine were added to 11, 33 or 100 nM and cultured for 72 hours and analyzed by flow cytometry for LSCs (a) and HSPCs (b) as in FIG. 1. Fold change before and after culture for each population is indicated relative to equivalent vehicle control concentrations.

Figure 11:
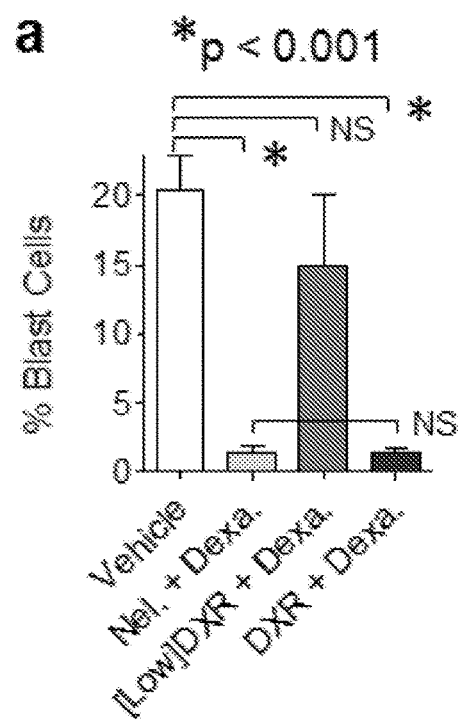

FIG. 11 illustrates normal dose DXR acts similar to chemotherapy in reducing blast cells but [Low]DXR does not. a, Leukemic mice established as described in FIG. 3a were treated with vehicle, chemotherapy (Nelarabine (Nel.)+dexamethasone (Dexa.)), [Low]DXR with Dexa., or normal dose DXR (8× higher than [Low]) with Dexa. At 10 days post-treatment, BM was analyzed by flow cytometry to determine frequency of blast cells. Average frequency±SD (n≥6 per group). Note that unlike FIG. 4, this experiment used normal or [Low] DXR as a substitute for Nelarabine but Dexamethasone treatment was retained in all groups due to the inability of single DNA damaging agents to effectively reduce blast cells. These data show that, even in combination with dexamethasone, [Low]DXR does not act as a traditional chemotherapeutic while normal DXR does.

Figure 12:
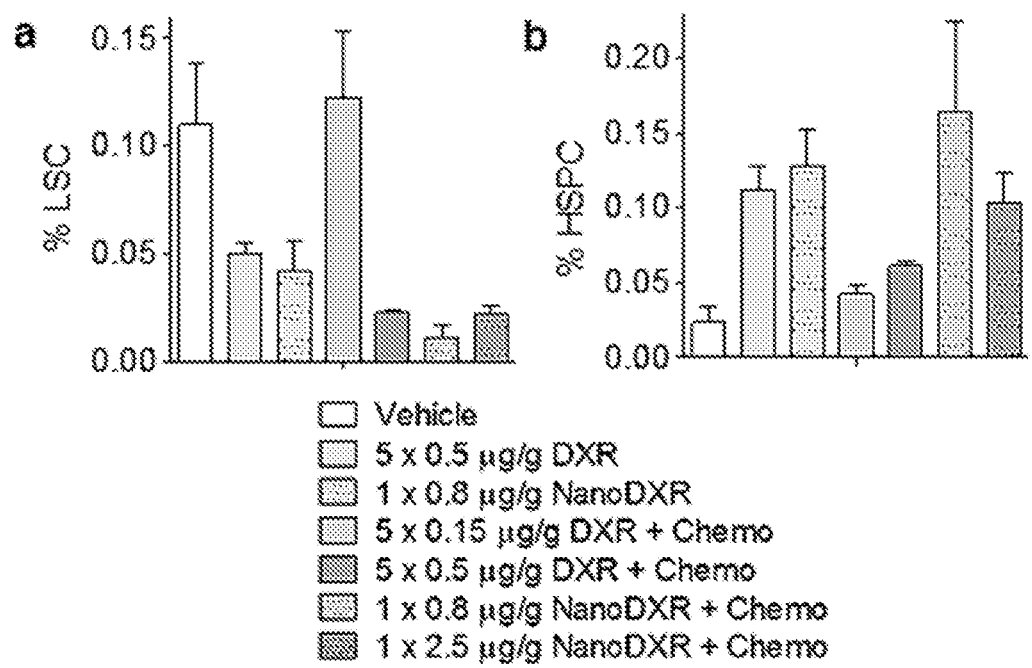

FIG. 12 shows single-dose DXR-loaded nanoparticles further reduce LSCs relative to free DXR in chemotherapy treated leukemic mice. a-b, Leukemic mice established as described in FIG. 3a were treated with 5 daily injections of free DXR at 0.5 or 0.15 µg/g with and without chemotherapy. Alternatively, a single injection on day 1 of 0.8 or 2.5 µg/g of DXR-loaded nanoparticles (NanoDXR) was given with and without chemotherapy. At 10 days post-treatment, BM was analyzed by flow cytometry to determine frequency of LSCs (a) and HSPCs (b). Shown is average frequency±SD (n≥6 per group). Note that 5 doses of 0.15 µg/g DXR is ineffective; however, a single NanoDXR injection with a similar cumulative dose (0.8 µg/g) is most effective at reducing LSCs while allowing for HSPC recovery.

Figure 5:
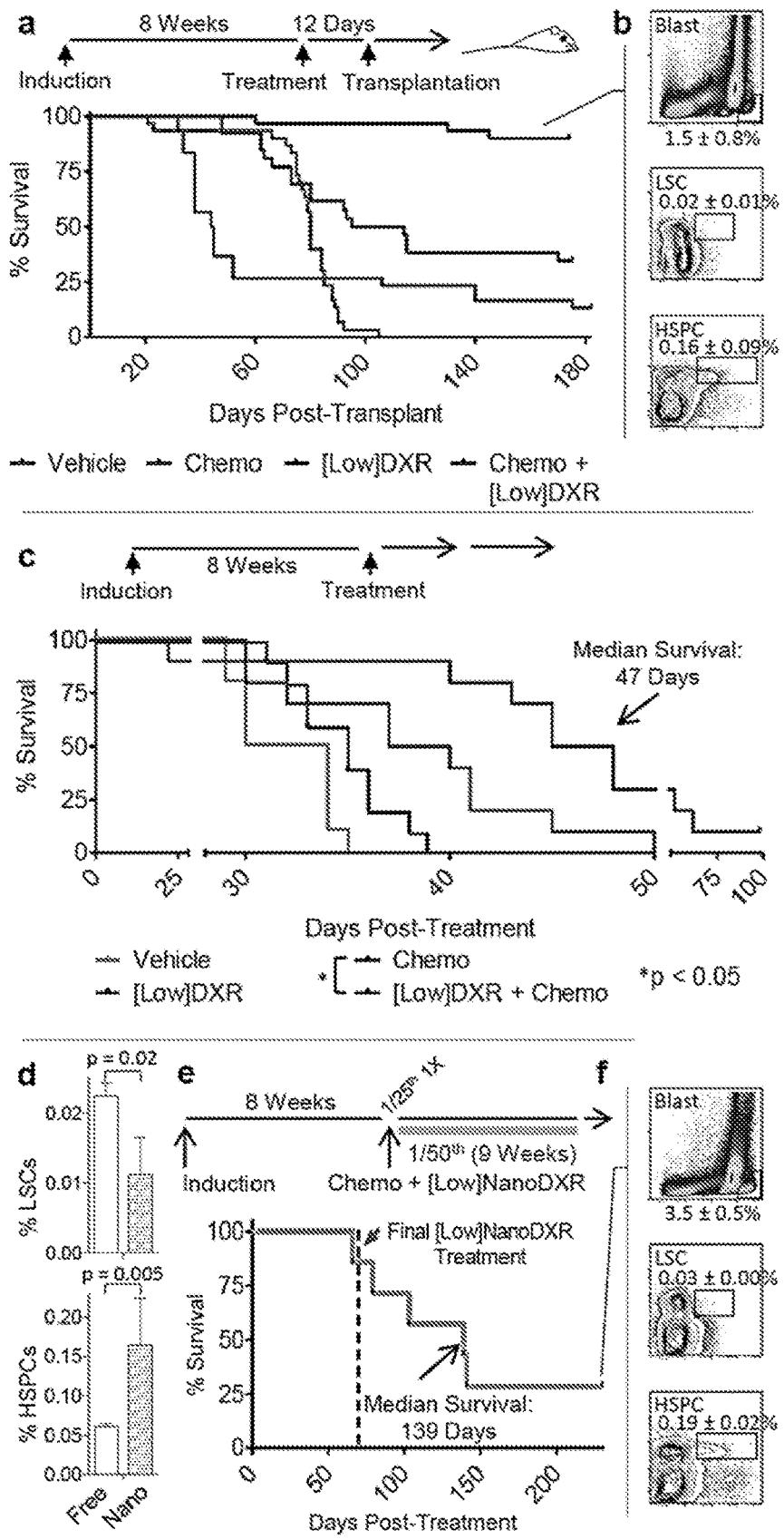
FIG. 5 illustrates chemotherapy induction combined with maintenance pS$^{552}$-β-catenin inhibition markedly improves therapeutic outcome. a, b, Cohorts of leukemic mice were treated with vehicle, chemotherapy, [Low]DXR or chemotherapy+[Low]DXR as in FIG. 3a. At 12 days post-treatment, BM was harvested from treated mice and transplanted into sub-lethally irradiated NSG recipients. a, Treatment schematic and Kaplan-Meier curves of recipient mice. b, Recipients of BM from [Low]DXR only treated leukemic mice were analyzed by flow cytometry at 6 months post-transplant. Shown are representative plots of blast cells, LSCs, and HSPCs with average frequency±SD of surviving 29/30 recipients from this group. c, Treatment schematic and Kaplan-Meier curves of mice treated as indicated after leukemia development. d, LSC and HSPC frequency in BM of leukemic mice at 10 days post-treatment with chemotherapy and either free [Low]DXR or [Low]nanoDXR. e, Treatment schematic and Kaplan-Meier curves of chemotherapy+ weekly [Low]nanoDXR treatment for 10 weeks total. Dashed line indicates day of final [Low]nanoDXR treatment. f, Surviving [Low]nanoDXR treated mice were analyzed by flow cytometry at 230 days post-treatment.
Figure 13:
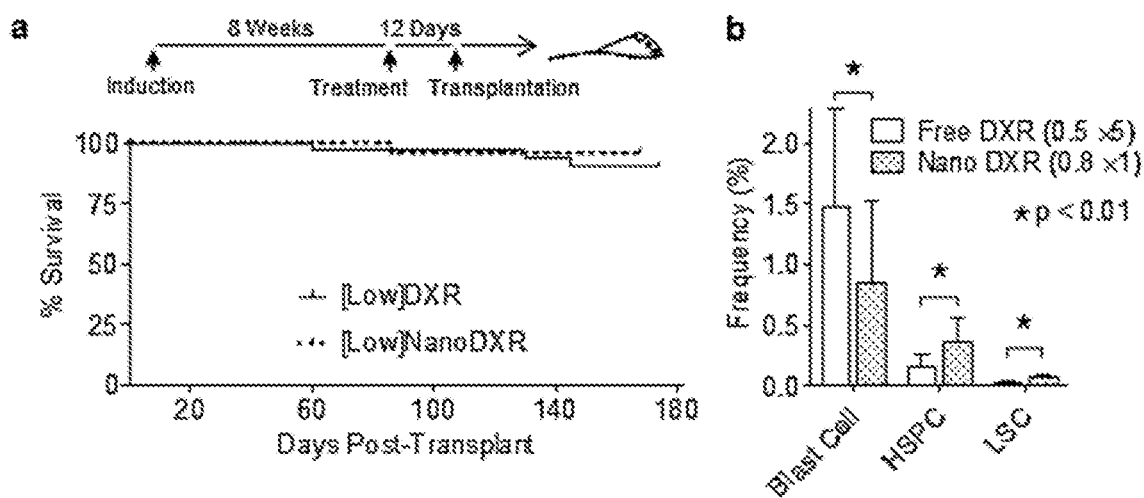

FIG. 13 illustrates that [Low]NanoDXR treatment reduces functional LSCs in vivo. a-b, Cohorts of leukemic mice were prepared and treated as in FIG. 3a but with [Low]NanoDXR. At 12 days post-treatment, BM was harvested from treated mice and transplanted into sub-lethally irradiated NSG recipients. a, Treatment schematic and Kaplan-Meier curves of recipient mice. The free [Low]DXR treatment group (solid line) from FIG. 5a is shown for comparison (n=30 per group). b, Recipients of BM from [Low]DXR and [Low]NanoDXR treated leukemic mice were analyzed by flow cytometry at 6 months post-transplant for Blast cells, HSPCs and LSCs (n=27-29 per group).

Figure 14:
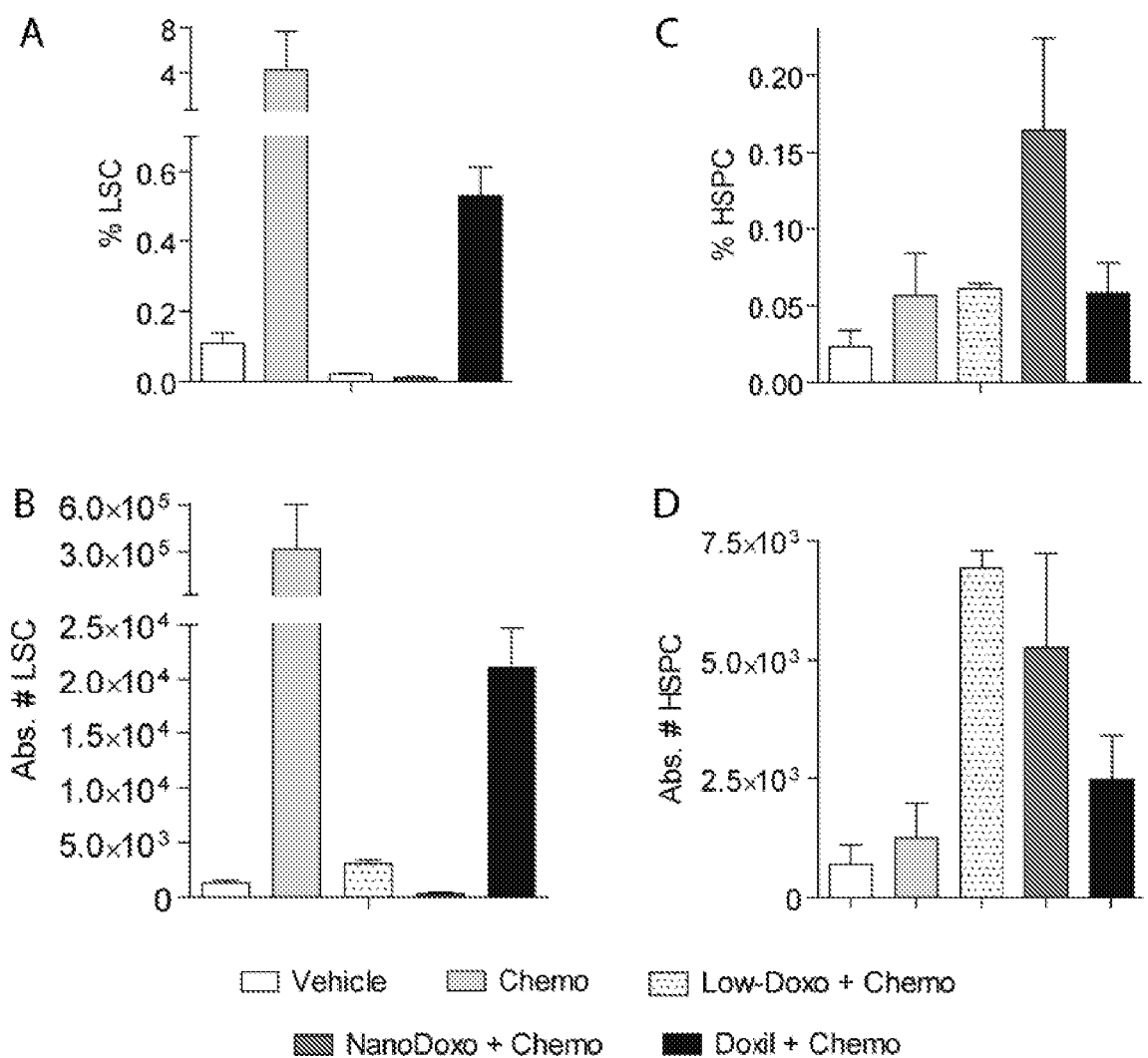

FIG. 14 illustrates that doxorubicin nanoparticles have enhanced effectiveness in eliminating leukemic stem cells and facilitating normal hematopoietic stem/progenitor cell recovery compared to Doxil®. Leukemic mice were injected with vehicle, chemotherapy, or chemotherapy combined with five daily low doses of doxorubicin (Doxo), nanoparticle encapsulated doxorubicin (NanoDoxo), or Doxil® (see Materials and Methods). Bone marrow was harvested 5-6 days after treatment and analyzed by flow cytometry for HSPCs (identified as lineage negative, Sca-1$^+$, c-Kit$^+$ cells) and LSCs (lineage negative, c-Kit$^{Mid}$, CD3$^+$ cells). LSCs and HSPCs were quantified by frequency (A, C) and absolute number per femur (B, D).

Figure 15:
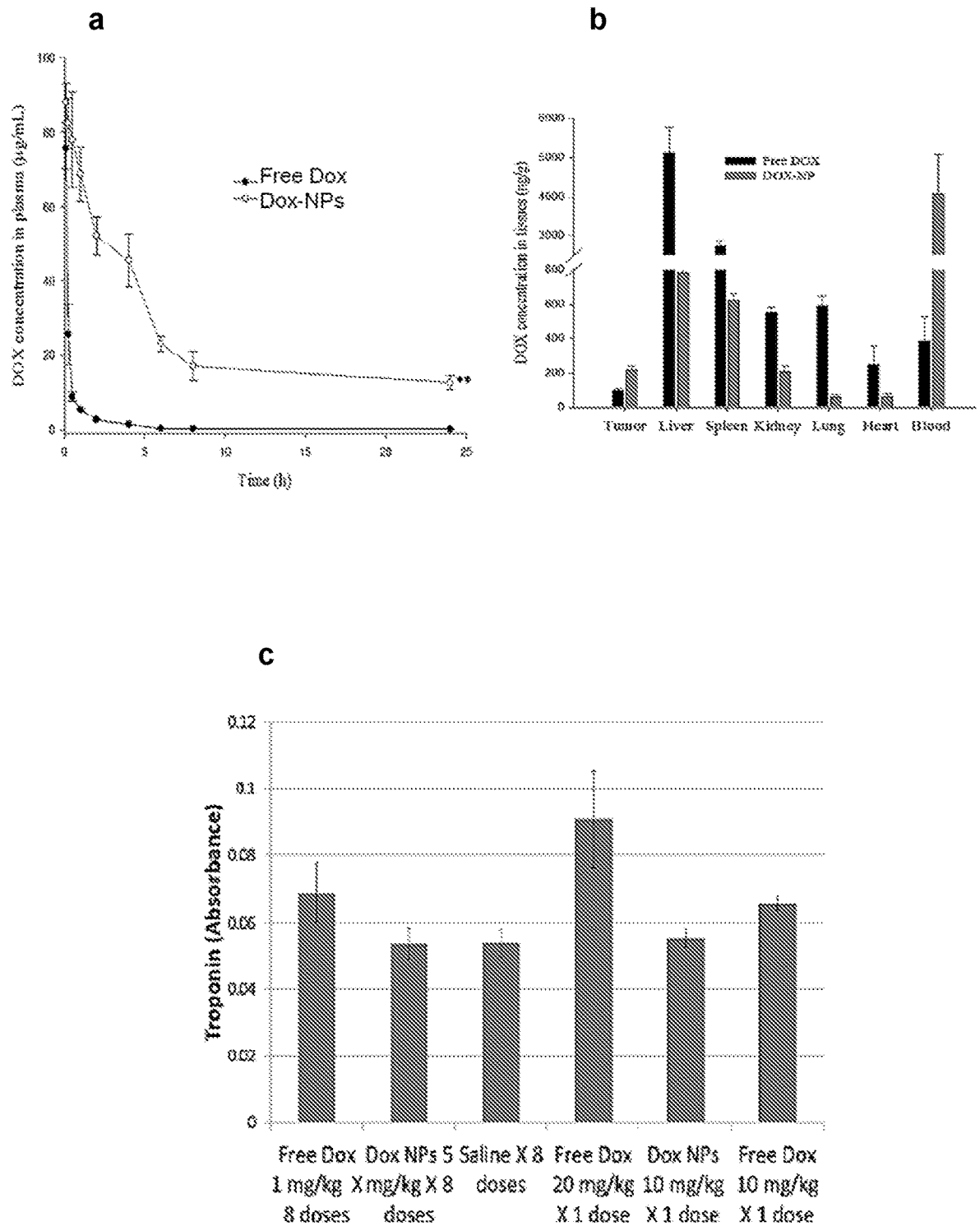

FIG. 15 provides a, in vivo circulation time of free doxorubicin (DOX) and doxorubicin nanoparticles (DOX-NPs). b, shows tissue distribution of DOX and DOX-NPs in tumor-bearing SCID mice after 24 h injection. Data are presented as mean±SD (n=5) *P<0.05, **P<0.01. c provides cardiac Troponin I level after administration of free doxorubicin (DOX) and doxorubicin nanoparticles (DOX-NPs).

DETAILED DESCRIPTION OF THE INVENTION

Before the disclosed methods and materials are described, it is to be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

In view of the present disclosure, the methods described herein can be configured by the person of ordinary skill in the art to meet the desired need. For example, in certain aspect, the disclosure provides methods of treating cancer, comprising administering to a subject in need thereof a pharmaceutically active molecule that is capable of selectively inhibiting p-S$^{552}$-β-catenin, p-T$^{217}$-β-catenin, p-T$^{332}$-β-catenin, and/or p-S$^{675}$-β-catenin production and/or activity, wherein the pharmaceutically active molecule is administered in an amount effective to reduce and/or limit cancer-initiating cells. In certain embodiments, the cancer is resistant to traditional treatment. For example, the cancer of the disclosure is resistant to radiation therapy, chemotherapy, immunotherapy, or any combination thereof.

In other embodiments, the cancer is selected from the group consisting of leukemia, lymphoma, prostate cancer, breast cancer, endometrial cancer, gastrointestinal cancer, lung cancer, melanoma, sarcoma, neuroblastoma, mesothelioma, testicular cancer, thyroid cancer, ovarian cancer, uterine cancer, pancreatic cancer, liver cancer, and Wilms' Tumor. In one embodiment, the cancer is leukemia.

In certain embodiments, the pharmaceutically active molecule is administered in a low dose and/or slow release and/or nanoparticle formulation. In one embodiment, the low dose is the dose at which the inhibitory effect of the pharmaceutically active molecule on known topoisomerase II-dependent cytotoxicity that requires higher dosage is reduced. For example, the low dose may be about ⅕ to about 1/50 of the clinical dose of the pharmaceutically active molecule when dosed for chemotherapy, wherein the clinical dose is the human dose approved for use in any country.

In certain embodiments, the low dose may be about ⅕ to about 1/40, or about ⅕ to about 1/30, or about ⅕ to about 1/25, or about ⅕ to about 1/20, or about ⅕ to about 1/15, or about ⅕ to about 1/10, or about ⅙ to about 1/50, or about 1/7 to about 1/50, or about 1/10 to about 1/50, or about 1/15 to about 1/50, or about 1/20 to about 1/50, or about 1/25 to about 1/50, or about 1/30 to about 1/50, or about 1/40 to about 1/50, 1/10 to about 1/40, or about 1/10 to about 1/30, or about 1/10 to about 1/25, or about 1/10 to about 1/20, or about 1/10 to about 1/15, 1/20 to about 1/40, or about 1/20 to about 1/30, or about 1/20 to about 1/25, or about 1/30 to about 1/40, or about 1/15 to about 1/25, or about 1/6 to about 1/30, or about 1/7 to about 1/30, or about 1/10 to about 1/30, or about 1/15 to about 1/30, or about 1/20 to about 1/30, or about 1/25 to about 1/30, or up to about 1/50, or up to about 1/40, or up to about 1/35, or up to about 1/30, or up to about 1/25, or up to about 1/20, or up to about 1/15, or up to about 1/10, or up to about ⅛, or up to about ⅙, or up to about ⅕, the clinical dose of the pharmaceutically active molecule when dosed for chemotherapy, wherein the clinical dose is the human dose approved for use in the U.S. or any other country.

In certain embodiments, the low dose may be about 0.01 to about 30 mg/m²/day of the pharmaceutically active molecule. In other embodiments, the low dose is from about 0.01 to about 25, or about 0.01 to about 20, or about 0.01 to about 15, or about 0.01 to about 10, or about 0.01 to about 9, or about 0.01 to about 7.5, or about 0.01 to about 5, or about 0.01 to about 3, or about 0.01 to about 2, or about 0.1 to about 30, or about 0.1 to about 25, or about 0.1 to about 20, or about 0.1 to about 15, or about 0.1 to about 10, or about 0.1 to about 9, or about 0.1 to about 7.5, or about 0.1 to about 5, or about 0.1 to about 3, or about 0.1 to about 2, or about 1 to about 30, or about 1 to about 25, or about 1 to about 20, or about 1 to about 15, or about 1 to about 10, or about 1 to about 9, or about 1 to about 7.5, or about 1 to about 5, or about 1 to about 3, or about 1 to about 2, or about 5 to about 30, or about 5 to about 25, or about 5 to about 20, or about 5 to about 15, or about 5 to about 10, or about 5 to about 9, or about 5 to about 7.5, or about 10 to about 30, or about 10 to about 25, or about 10 to about 20, or about 10 to about 15, or about 15 to about 30, or about 15 to about 25, or about 15 to about 20, or about 20 to about 30, or up to about 0.01, or from about 0.01 and up to about 0.05, or up to about 0.1, or up to about 0.5, or up to about 1, or up to about 2, or up to about 3, or up to about 4, or up to about 5, or up to about 6, or up to about 7, or up to about 8, or up to about 9, or up to about 10, or up to about 15, or up to about 20, or up to about 25, or up to 26, or up to 28, or up to 30, mg/m²/day of the pharmaceutically active molecule. In non-limiting example, doxorubicin may be administered at a dose of about 7 to about 8, or about 7.5 to about 8.5 mg/m²/day. In non-limiting example, doxorubicin may be administered at a dose of up to about 10 mg/m²/day. In non-limiting example, doxorubicin nanoparticles may be administered at a dose of about 2 to about 3, or about 2.4 5 mg/m²/week (e.g., about 0.34 mg/m²/day).

In certain embodiments, the low dose may be about 20 to about 50 mg/m²/day of the pharmaceutically active molecule. In other embodiments, the low dose is from about 25 to about 50, or about 30 to about 50, or about 40 to about 50, or about 20 to about 45, or about 20 to about 40, or about 25 to about 45, or up to about 50, or up to about 45, or up to about 40, or up to about 35, mg/m²/day of the pharmaceutically active molecule.

In certain embodiments, the pharmaceutically active molecule is anthracycline or a pharmaceutically acceptable salt thereof. Anthracyclines are a class of compounds derived from Streptomyces bacterium. Examples include, but are not limited to, doxorubicin, daunorubicin, epirubicin, idarubicin, valrubicin, and mitoxantrone. In one embodiment, the pharmaceutically active molecule is doxorubicin or daunorubicin. In another embodiment, the pharmaceutically active molecule is daunorubicin or a pharmaceutically acceptable salt thereof. In yet another embodiment, the pharmaceutically active molecule is doxorubicin or a pharmaceutically acceptable salt thereof.

In certain embodiments, the pharmaceutically active molecule is hydrophobic molecule.

In certain embodiments, the pharmaceutically active molecule is any one of compositions disclosed in International Publication No. WO 2015/054269 and International Publication No. WO 2016/061310, both incorporated herein by reference in their entirety.

The methods of the disclosure, in one aspect, may comprise administration of the pharmaceutically active molecule in a nanoparticle form (e.g., core/shell nanoparticle form). Such nanoparticles are able to encapsulate large amount of hydrophobic drug molecules into the nanoparticles during the self-assembling process. The hydrophilic surface protects the nanoparticles from reticuloendothelial system (RES) uptake and facilitates long circulation in body. Furthermore, the nanoparticles significantly increased the duration of the drug in the circulation and decreased cardiac accumulation of the drug. Finally, the nanoparticles of the disclosure may be used for intracellular delivery of anticancer drugs with minimal toxicity.

In some embodiments, wherein the pharmaceutically active molecule as described above is administered in one or more nanoparticle compositions comprising a block copolymer in a core/shell form, wherein the block copolymer comprises:

a first block, which is of formula:

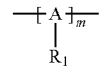

and a second block, which is of formula:

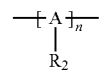

wherein m and n are independently an integer about 3 to about 500;

A is independently selected from polynorbonene, polycyclopentene, polycyclooctene, polyacrylate, polymethacrylate, a polysiloxane, polylactide, polycaprolactone, polyester, and polypeptide;

$R_1$ is a steroid moiety optionally comprising a linker; and $R_2$ is a polyalkylene oxide moiety.

The block copolymers useful in the methods of the disclosure require that $R_1$ comprises a steroid moiety optionally comprising a linker. As the person of ordinary skill in the art will appreciate, suitable steroids may be selected to meet the desired need. For example, the steroid moiety suitable in the materials of the disclosure comprises cholesterol, cholic acid, deoxycholic acid, taurocholic acid, lanosterol, estradiol, testosterone, bile acid, dexamethasone, secosteroid, or phytosterol. In some embodiments, the steroid moiety comprises cholesterol, cholic acid, deoxycholic acid, taurocholic acid or the like. In one embodiment, the steroid moiety comprises cholesterol.

The steroid moiety may be connected to the polymer backbone via a suitable linker. Some examples of linkers include, but are not limited to:

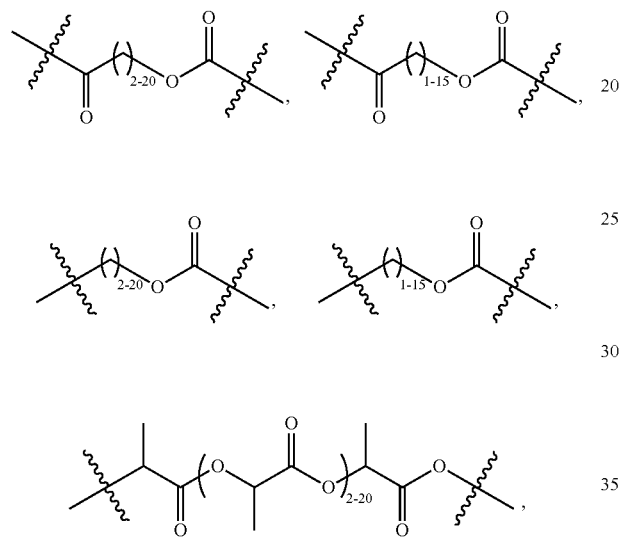

polylactone, or an oligomer of siloxane. In one embodiment, the linker at $R_1$ is:

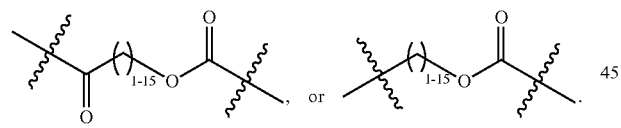

In another embodiment, the linker at $R_1$ is:

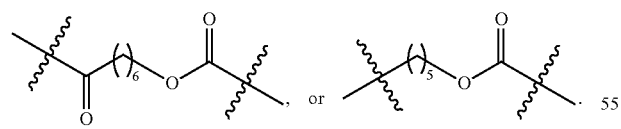

The block copolymers useful in the methods of the disclosure require that $R_2$ comprises a polyalkylene oxide moiety. As the person of ordinary skill in the art will appreciate, suitable polyalkylene oxides may be selected to meet the desired need. In some embodiments, the polyalkylene oxide moiety comprises polyethylene oxide or polyethylene oxide thiolate. In another embodiment, the polyalkylene oxide moiety comprises polyethylene oxide.

The block copolymers useful in the methods of the disclosure require a backbone moiety A. The block copolymers described herein may contain, for example, polynorbonene, polycyclopentene, polycyclooctene, polyacrylate, polymethacrylate, and a polysiloxane backbone A available to one skill in the art, and may be varied depending on the desired product. In one embodiment, the block copolymers of disclosure are those wherein each A is independently polynorbonene or polyacrylate. In another embodiment, each A is independently polynorbonene. In another embodiment, each A is independently polyacrylate.

In one embodiment, the block copolymers useful in the methods of the disclosure comprise the structure:

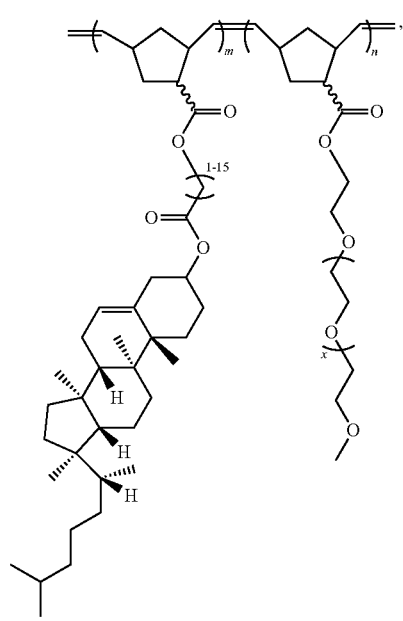

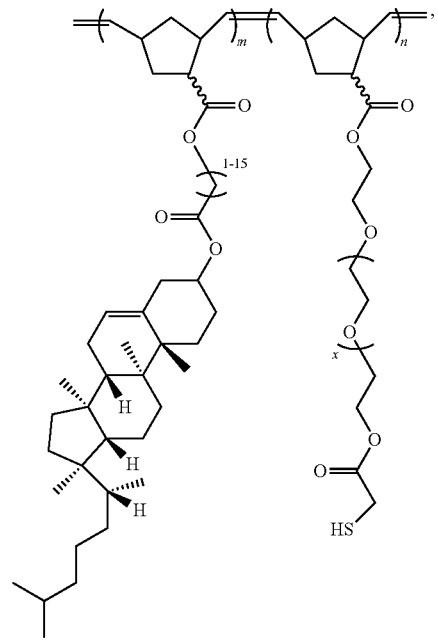

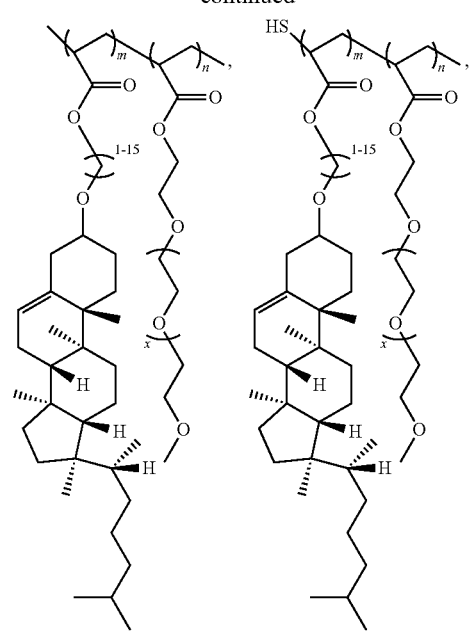
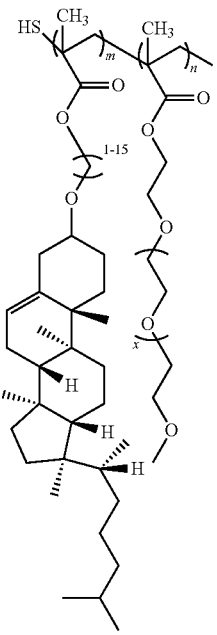
, or
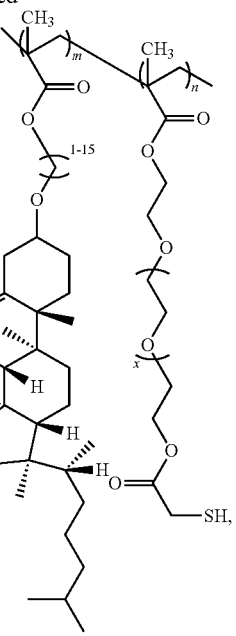

wherein x is an integer between about 3 and about 100; m is an integer between about 5 and about 200; and n is an integer between about 5 and about 100. In some embodiments, x is between about 5 and 50. In other embodiments, x is about 8, or x is about 44.

The values of m and n may be selected by one of skill in the art and may be varied depending on the desired product. For example, m may be between about 10 and about 100; and/or n may be between about 15 and about 85. The molecular weight of the block copolymer of the disclosure may be between about 10,000 and about 1,000,000 Da. In one embodiment, the block copolymer of the disclosure is about 40,000 to about 750,000 Da, or about 60,000 to about 700,000 Da, or about 60,000 to about 100,000 Da, or about 40,000 to about 200,000 Da.

In some other embodiments, wherein the pharmaceutically active molecule as described above is administered in one or more nanoparticle compositions comprising a block copolymer in a core/shell form, wherein the block copolymer comprises:

a first block, which is of formula:

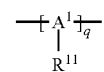

and a second block, which is of formula:

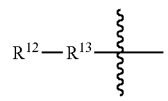

wherein
q is an integer about 3 to about 500;
$A^1$ is independently selected from polyacrylate, polymethacrylate, polynorbonene, polycyclopentene, polycyclooctene, polysiloxane, polylactide, polycaprolactone, polyester, and polypeptide;

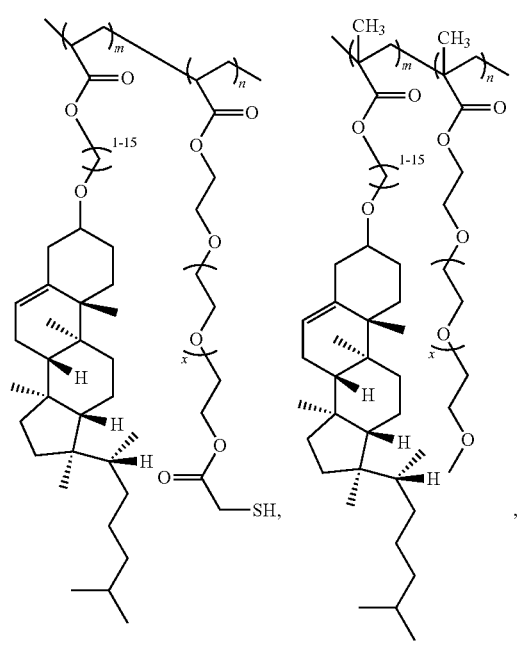

$R^{11}$ is a steroid moiety optionally comprising a linker $R^{14}$;

$R^{12}$ polyalkylene oxide, polyester, or polypeptide moiety; and $R^{13}$ is a disulfide linker moiety.

In some embodiments, the steroid moiety in $R^{11}$ comprises cholesterol, cholic acid, deoxycholic acid, taurocholic acid, lanosterol, estradiol, testosterone, bile acid, dexamethasone, secosteroid, phytosterol, or the like. In another embodiment, the steroid moiety in $R^{11}$ is selected from cholesterol, cholic acid, deoxycholic acid, and taurocholic acid. In another embodiment, the steroid moiety in $R^{11}$ comprises cholesterol.

The steroid moiety may be connected to the polymer back bone via a suitable linker $R^{14}$. Some examples of linker $R^{14}$ include, but are not limited to:

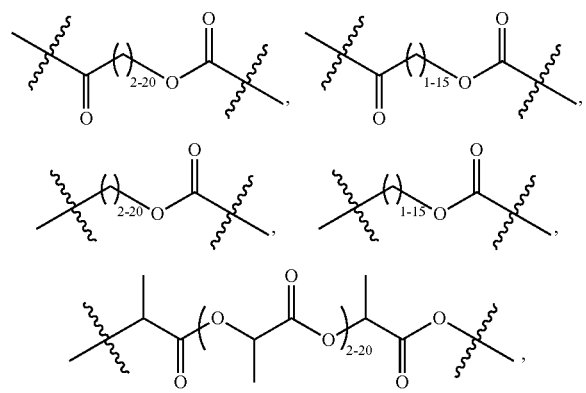

polylactone, or an oligomer of siloxane. In one embodiment, the linker at $R^{14}$ is

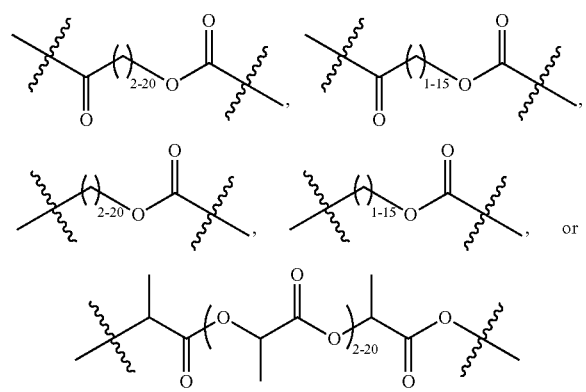

In another embodiment, the linker at $R^{14}$ is:

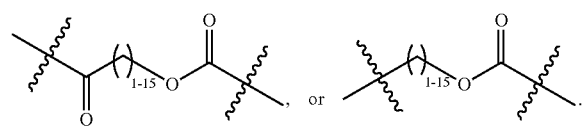

In another embodiment, the linker at $R^{14}$ is

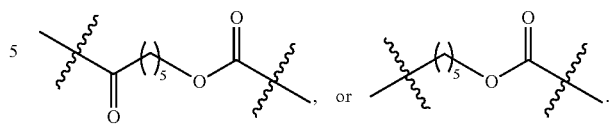

In one embodiment, the linker at $R^{14}$ is

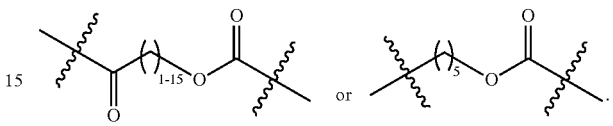

In one embodiment, the block copolymers useful in the methods of disclosure are those wherein each $A^1$ is independently polyacrylate, polymethacrylate, or polyester. In another embodiment, each A is independently polyacrylate or polymethacrylate. In another embodiment, each $A^1$ is independently polyacrylate. In another embodiment, each $A^1$ is independently polymethacrylate. In another embodiment, each $A^1$ is independently polyester.

In an exemplary embodiment, the first block is of formula:

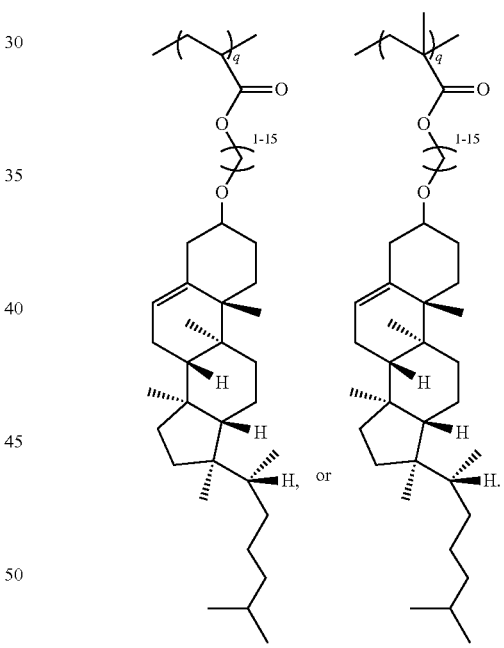

In one embodiment, $R^{12}$ is polyalkylene oxide moiety. Suitable polyalkylene oxides may be selected to meet the desired need. In some embodiments, the polyalkylene oxide moiety comprises polyethylene oxide, polyethylene oxide thiolate, polypropylene oxide, or polypropylene oxide thiolate. In another embodiment, the polyalkylene oxide moiety comprises polyethylene oxide or polyethylene oxide thiolate. In another embodiment, the polyalkylene oxide moiety comprises polyethylene oxide.

In one embodiment, $R^{12}$ is polyester moiety. Suitable polyesters include polymers that contain the ester functional group in their main chain. Examples include, but are not limited to, polylactides, polyglycolides, polycaprolactones, and the like.

In one embodiment, $R^{12}$ is polypeptide moiety. Suitable polypeptides include one or more chains of amino acid monomers linked together by peptide (amide) bonds, and may comprise L-amino acids, D-amino acids (which are resistant to L-amino acid-specific proteases in vivo), or a combination of D- and L-amino acids. Typically, polypeptides described herein refer to a chain less than about 100 amino acids in length. The polypeptides described herein may be chemically synthesized or recombinantly expressed.

The second block also comprises $R^{13}$ linker moiety comprising reducible disulfide bonds. In one embodiment, $R^3$ is selected from the group consisting of:

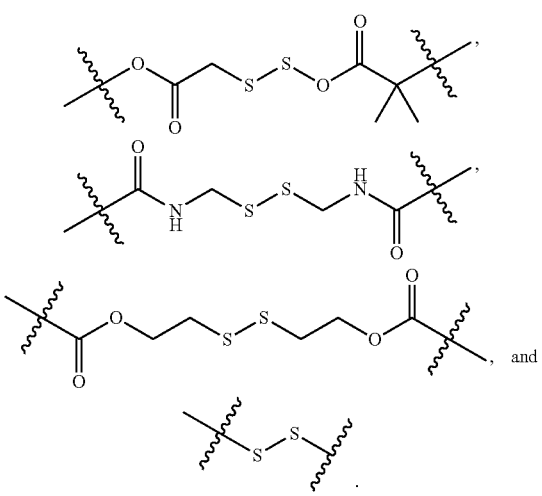

In one embodiment, $R^{13}$ is

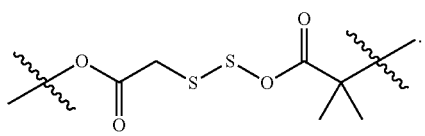 [SMILES: *OC(=O)CSSOC(=O)C(*)(C)C]

In another embodiment, $R^{13}$ is derived from

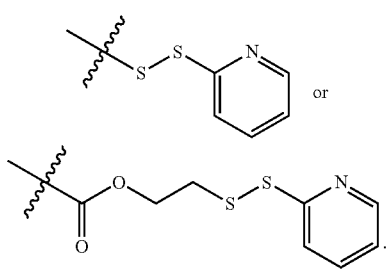

In certain embodiment, the copolymer of the disclosure may further comprise a chain terminus moiety X:

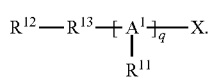

In one embodiment, X is a trithiocarbonate, dithiocarbamate, or dithioester. In another embodiment, X is —SC(S)S—($C_1$-$C_{24}$ alkyl). In another embodiment, X is —SC(S)S—$C_{12}H_{25}$.

In one embodiment, the block copolymers useful in the methods of the disclosure comprise the structure:

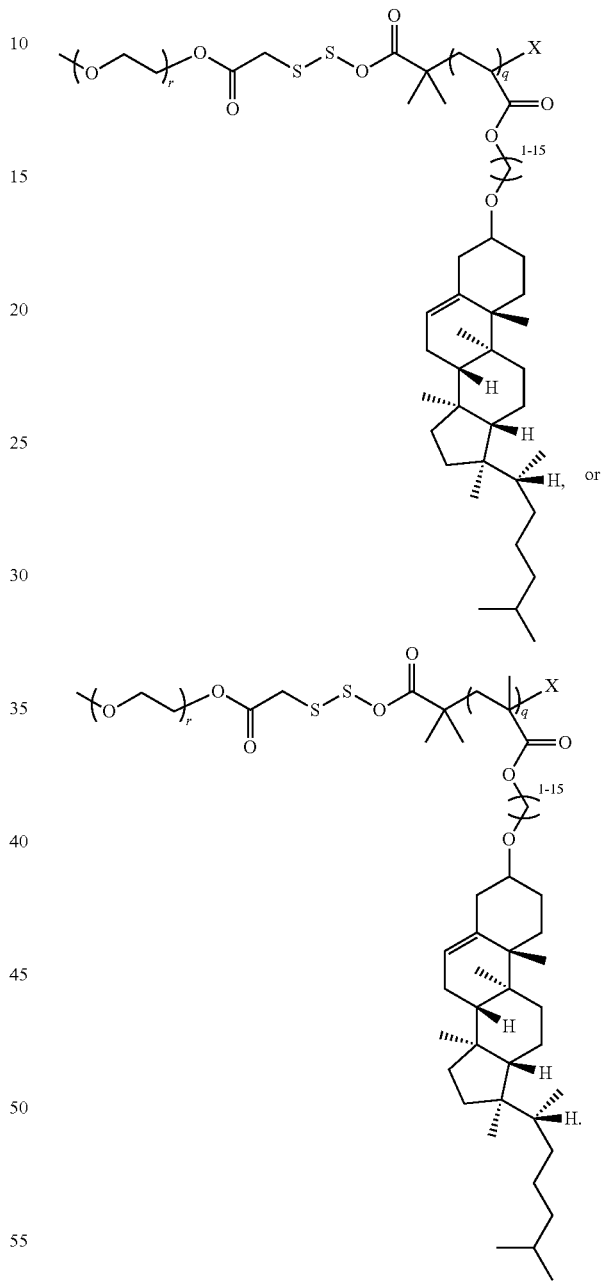

wherein q is an integer between about 5 and about 200; and r is an integer between about 5 and about 100.

The values of q and r may be selected by one of skill in the art and may be varied depending on the desired product. For example, q may be between about 10 and about 100; and/or r may be between about 15 and about 85. The molecular weight of the block copolymer of the disclosure may be between about 5,000 to about 200,000 Da. In one embodiment, the block copolymer of the disclosure is about 5,000 to about 150,000 Da, or about 5,000 to about 100,000 Da, about 5,000 to about 60,000 Da, or about 10,000 to about 150,000 Da, or about 10,000 to about 100,000 Da, or about 10,000 to about 60,000 Da, or about 20,000 to about 150,000 Da, or about 20,000 to about 100,000 Da, or about 20,000 to about 60,000 Da.

In one embodiment, the methods of the disclosure comprise administration of the pharmaceutically active molecule in a combination of two different nanoparticle compositions. In some embodiments, a first nanoparticle composition comprises the hydrophobic pharmaceutically active molecule that is doxorubicin. In other embodiments, a second nanoparticle composition comprises the hydrophobic pharmaceutically active molecule selected from the group consisting of daunorubicin, vincristine, epirubicin, idarubicin, valrubicin, mitoxantrone, paclitaxel, docetaxel, cisplatin, camptothecin, irinotecan, 5-fluorouracil, methotrexate, or dexamethasone. In some other embodiments, a second nanoparticle composition comprises the hydrophobic pharmaceutically active molecule selected from daunorubicin and epirubicin.

The nanoparticles useful in the methods of the disclosure may further comprise one or more of metal nanoparticles, such as gold nanoparticles and/or magnetic nanoparticles and/or quantum dots (for example, near infrared (NIR) quantum dot, CdSe and the like).

The nanoparticles useful in the methods of the disclosure of the disclosure may be anywhere from about 5 to about 900 nm in size. For example, the nanoparticles may be between about 5 and about 200 nm, or between about 10 and about 100 nm, or between about 10 and about 200 nm, or between about 50 and about 150 nm, or between about 100 and about 250 nm, or between about 100 and about 200 nm, or between about 120 and about 150 nm, or between about 110 and about 150 nm, or between about 120 and about 180 nm, or between about 150 and about 250 nm, or between about 150 and about 200 nm.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. In some embodiments, the term "about" means±10% of the recited value. In another embodiment, term "about" means±5% of the recited value.

The term "activity," for example of a protein, as used herein includes direct activity of that protein and indirect downstream activity of that protein. For example, interaction with the protein 14-3-3zeta results in stabilization of β-catenin, enhanced nuclear localization of β-catenin, enhanced binding/activity to TCF/LEF transcription factor sites, or activation of a molecular program resulting in stem cell proliferation.

The term "cancer-initiating cells" (CICs), e.g., "cancer stem cells" (CSCs), as used herein include cells that have the ability to generate or regenerate tumors. In certain embodiments CICs are resistant to standard chemotherapeutic treatment.

As used herein the term "combining" includes adding one or more items to a reaction mixture.

As used herein the term "dispersity," "polydispersity," "polydispersity index", "PDI," and "$M_w/M_n$" are used interchangeably and refer to measure of the polymer uniformity with respect to distribution of molecular mass. The dispersity may be calculated by dividing weight average molecular weight ($M_w$) by the number average molecular weight ($M_n$) (i.e., $M_w/M_n$). In certain embodiments, the dispersity may be calculated according to degree of polymerization, where the dispersity equals $X_w/X_n$, where $X_w$ is the weight-average degree of polymerization and $X_n$ is the number-average degree of polymerization.

All percentages, ratios and proportions herein are by weight, unless otherwise specified. A weight percent (weight %, also as wt %) of a component, unless specifically stated to the contrary, is based on the total weight of the composition in which the component is included (e.g., on the total amount of the reaction mixture).

The terms "reduce and/or limit cancer-initiating cells" includes any amount of absolute reduction (about 5%, about 10%, about 25%, about 50%, about 75%, about 95%, or greater, or complete elimination) of cancer-initiating cells, and any amount of limiting the rate of expansion about 5%, about 10%, about 25%, about 50%, about 75%, about 95%, or greater) as compared to cells receiving no treatment.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment of a disease or disorder described herein, in a subject, preferably a human, and includes:

i. inhibiting a disease or disorder, i.e., arresting its development;

ii. relieving a disease or disorder, i.e., causing regression of the disorder;

iii. slowing progression of the disorder; and/or iv. inhibiting, relieving, or slowing progression of one or more symptoms of the disease or disorder.

"Subject" refers to a warm blooded animal such as a mammal, preferably a human, or a human child, which is afflicted with, or has the potential to be afflicted with one or more diseases and disorders described herein.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

The term "polyester" as used herein includes polymers that contain the ester functional group in their main chain. Non-limiting examples include polylactides, polyglycolides, polycaprolactones, and the like. The term "polypeptide" as used herein includes a chain of amino acid monomers linked together by peptide (amide) bonds, and may comprise L-amino acids, D-amino acids (which are resistant to L-amino acid-specific proteases in vivo), or a combination of D- and L-amino acids. Typically, polypeptides described herein refer to a chain less than about 100 amino acids in length. The polypeptides described herein may be chemically synthesized or recombinantly expressed.

EXAMPLES

The materials and methods of the disclosure are illustrated further by the following examples, which are not to be construed as limiting the disclosure in scope or spirit to the specific procedures and materials described in them.

Materials and Methods

Animals

Mice were housed in the animal facility at Stowers Institute for Medical Research (SIMR) and handled according to Institute and NIH guidelines. All procedures were approved by the IACUC of SIMR. The HSC-SCL-Cre-ER$^T$ Pten$^{loxP/loxP}$ βcat(Ctnnb1)$^{loxP(Exon3)/+}$ (hereafter, Pten:β-cat$^{Act}$) mouse model combines conditional deletion of LoxP flanked Pten, resulting in activation of the PI3K/Akt pathway, and exon 3 of β-catenin (β-cat$^{Act}$), resulting in constitutive activation of β-catenin. The hematopoietic stem/progenitor cells (HSPCs)-specific Cre recombinase, HSCSCL-Cre-ER$^T$, was used to study of the combined effects of both pathways starting with HSPCs and without the HSC activating effects of induction by interferon. Primary HSC-SCL-Cre mice were induced by intra-peritoneal injection of tamoxifen daily for 5 days using 5 mg on day 1 and 2 mg on days 2-5 each dissolved in 0.1 ml of corn oil. A Bioruptor® sonicator was used to fully solubilize the tamoxifen. HSC-SCL-Cre was induced in transplant recipients by placing transplant recipients on tamoxifen feed (1 mg/g) for 2 weeks. HSC-SCL-Cre, Pten, and β-cat$^{Act}$, were obtained from Joachim Goethert (University of Duisburg-Essen, Germany), Hong Wu (UCLA, Los Angeles, Calif.), and Makoto Taketo (Kyoto University, Japan), respectively.

Transplantation Assays

Whole bone marrow was isolated from uninduced HSC-SCL-Cre$^+$ Pten$^{fx/fx}$ βcat$^{fx(Exon3)/+}$ (Pten:β-cat$^{Act}$) mice and combined with an equal portion of Cre negative bone marrow from a littermate and transplanted into irradiated (10 Gy) B6.SJL-Ptprc$^a$ Pepc$^b$/BoyJ (Ptprc) recipients. Recipients were placed on Tamoxifen feed 4-6 weeks post-transplant to induce recombination, resulting in leukemia development by 7-8 weeks post-induction in all recipient mice.

Limiting-dilution and tumorigenic assays were performed by establishing leukemic mice as described above and treating as indicated at 8 weeks post-induction. For limiting-dilution transplants, mice were treated with chemotherapy or [Low]DXR and, at 10 days post-treatment (based on first treatment), CD45$^{Hi}$ CD3$^+$ c-Kit$^-$ blast cells or Lin$^-$ CD3$^+$ c-Kit$^{Mid}$ LSCs were sorted from chemotherapy treated mice and Lin$^-$ Sca-1$^+$ c-Kit$^+$ HSPCs were sorted from [Low]DXR treated mice. The indicated numbers of these populations were transplanted into 3.25 Gy irradiated NOD.Cg-Prkdc$^{scid}$ Il2rg$^{tm1Wjl}$/SzJ (NSG) recipient mice. Recipient bone marrow was analyzed by flow cytometry at 10-12 weeks post-transplant and those with ≥1% CD45$^{Hi}$ blast cells in bone marrow were considered engrafted. CRU frequency was determined using ELDA analysis.

Tumorigenic assays were performed by transplanting 0.5, 1.5, or 4.5×10$^4$ bone marrow cells from treated mice at 12 days post-treatment into 3.25 Gy irradiated NSG recipient mice. 10 recipients were used for each dose from each mice. One male and one female donor was used for each group. Leukemia was assessed in mice euthanized due to poor health by analyzing CD45$^{Hi}$ CD3$^+$ cell frequency. Mice having >20% Blasts in the bone marrow were considered leukemic. NSG and Ptprc mice were originally obtained from The Jackson Laboratory.

In Vitro Treatment

Bone marrow cells from leukemic mice at 8 weeks post-induction were cultured overnight at 5-20×10$^4$ cells per well in 96-well U-bottom tissue culture plates (Becton, Dickinson and Company; Cat. No. 353077) in HSC expansion media in low O$_2$ conditions as previously described (Perry, J. M. et al. Cooperation between both Wnt/{beta}-catenin and PTEN/PI3K/Akt signaling promotes primitive hematopoietic stem cell self-renewal and expansion. *Genes Dev* 25, 1928-1942 (2011)). Doxorubicin (Sigma; D1515), 0105375 ((S)-N-(2-bromobenzyl)-N-(1-hydroxy-3-phenyl-propan-2-yl)ethenesulfonamide, University of Kansas CMLD compound), or Thioguanosine was mixed with HSC expansion media and added to the cultures to obtain final concentrations of 11, 33, 100 nM. Equivalent amounts of DMSO alone (vehicle control) were added to parallel cultures for comparison. Half-media changes were performed approximately every 24 hrs. Cultures were analyzed after 72 hrs exposure to the indicated drug.

In Vivo Treatment

Chemotherapy consisted of Nelarabine (Selleck) and Dexamethasone (BioVision) administered daily for 5 days consecutively. 43.4 mg/ml Nelarabine was administered intravenously via the tail vain according to the formula: Body Weight (g)×5=volume to inject (µl), which yielded 217 mg/kg. 2.5 mg/ml Dexamethasone was injected intraperitoneally according to the formula: Body Weight (g)×4=volume to inject (µl), yielding 10 mg/kg. [Low]DXR (also referred to as [Low]Doxo or throughout) treatment consisted of 5 consecutive daily doses at 0.5 mg/kg using Doxorubicin hydrochloride (Sigma; D1515) at 0.1 mg/ml injected intravenously via the tail vain according to the formula: Body Weight (g)×5=volume to inject (µl), which yielded 0.5 mg/kg. [Low]NanoDXR (also referred to as [Low]Nano-Doxo throughout) treatment used doxorubicin nanoparticles as described in International Patent Publication WO 2015/054269 (incorporated by reference in its entirety) administered as a single IV injection once per week on day 1 relative to above treatments using 0.8 mg/kg. Maintenance [Low]NanoDXR consisted of once per week injections of 0.4 mg/kg. Groups combining Nelarabine with Doxorubicin used a single injection containing both drugs. All drugs were solubilized in 45% (2-Hydroxypropyl)-β-cyclodextrin (HBC).

Rationale for doxorubicin dosage: for clinical ALL therapy, doxorubicin is typically administered at a single dose every 21-28 days at 40-75 mg/m$^2$. Using 60 mg/m$^2$ as the clinical equivalent dose, this is equivalent to 1.6 mg/kg for adult humans (60 mg/m$^2$×1 m$^2$/37 kg=1.6 mg/kg). Converting to mouse, this is equivalent to ~20 mg/kg (1.6 mg/kg×12.3 (k$_{m(Human)}$/k$_{m(Mouse)}$)=19.7 mg/kg) (Freireich, E. J. et al., Quantitative comparison of toxicity of anticancer agents in mouse, rat, hamster, dog, monkey, and man. *Cancer chemotherapy reports. Part 1* 50, 219-244 (1966).).

Cumulatively, 2.5 mg/kg doxorubicin was administered and thus ⅛ the equivalent clinical dose spread over 5 days.

Flow Cytometry

Cells were collected from bone marrow (femur and tibia), spleen, peripheral blood, and thymus. For cell surface phenotyping, a lineage cocktail (Lin) was used including CD3 (for HSPC but not LSC analysis), CD4, CD8, Mac-1, Gr1, B220, IgM, and Ter119 (eBioscience, San Diego, Calif.). Monoclonal antibodies against CD3 (separate fluorophore for LSC analysis), Sca-1, c-Kit, CD45.1, and CD45.2 were also used where indicated. Cell sorting and analysis were performed using an inFlux (BD), MoFlo (Dako, Ft. Collins, Colo.) and/or CyAn ADP (Dako, Ft. Collins, Colo.). Data analysis was performed using FlowJo software (Ashland, Oreg.).

Immunostaining

Cells were sorted onto lysine-coated slides, fixed with methanol, blocked using Universal Block, and stained for pS552-β-catenin at 1:50 dilution.

FRET Assay

FRET measurement was performed by using the acceptor photobleaching method. Briefly, 293T cells were transfected with EGFP-AKT and mCherry-β-catenin (Addgene, #39531, #55001). A Perkin-Elmer Ultraview spinning disc system with a CSU-X1 Yokogawa disc was used for imaging. A 40X 1.2 NA Plan-apochromatic objective was used, and emission was collected onto a C9100 Hamamatsu Photonics EM-CCD. EGFP was excited with a 488 nm laser, and emission was collected through a 500-555 nm band pass filter. mCherry was illuminated, and photobleached, with a 561 nm laser. Emission of mCherry was collected with a 580-650 nm band pass filter. 6 images of EGFP were acquired before and 8 images after bleaching of the mCherry with intense 561 nm light. After subtraction of camera background, the average intensity of EGFP in a region of interest spanning the bleached cell was determined in the 4 images before acceptor bleach (I1), or the 4 images after acceptor bleach (I2). FRET efficiency is reported as 1−(I1/I2). Calculations were based on >500 cell images.

High-Throughput Screening 243 compounds were selected from primary screening of the validation library (5040 compounds) drawn from CMLD (1920), Prestwick (1120) and MicroSource Spectrum (2000) and reconfirmed in a 10 concentration dose-response. Activity of compounds was tested against HEK-TOP cells vs. HEK FOP cells for inhibition of luciferase activity. The cytotoxicity profiles of the compounds were also tested using Cell Titer Glo assay (Promega) on HEK-TOP cell lines. The dose-response data was used to calculate the EC50 (Effective concentration of compounds resulting in 50% inhibition of luminescence or cytotoxicity) using non-linear regression analysis. Approximately 90 compounds showed from 2.2 to 3 fold differences in EC50 between the TOP and FOP cells. Of these 36 compounds showed a window between luminescence inhibition and cytotoxicity. The structures of compounds were analyzed by cheminformatics analysis and medicinal chemists identified 25 compounds for repurchasing as fresh powders. The repurchased compounds were used to treat the cells at compound concentrations that resulted in 90%, 50% and 25% inhibition of luminescence(EC50, EC50 and EC25), derived from the dose-response curves for luminescence inhibition in HEK Top cell line. The HEK cells and HEK Top cells were plated at 300,000 cells/well in 6 well plates and were treated in duplicate with EC90, EC50 and EC25 concentrations of the 25 repurchased compounds as well as three controls. After 48 h of exposure, the cells were washed with PBS and flash frozen. The frozen cells were lysed directly in plates for Western analysis.

Statistical Analyses

Data expressed as mean±standard deviation. Pair-wise comparisons performed using Student's t-test.

Example 1

Figure 6:
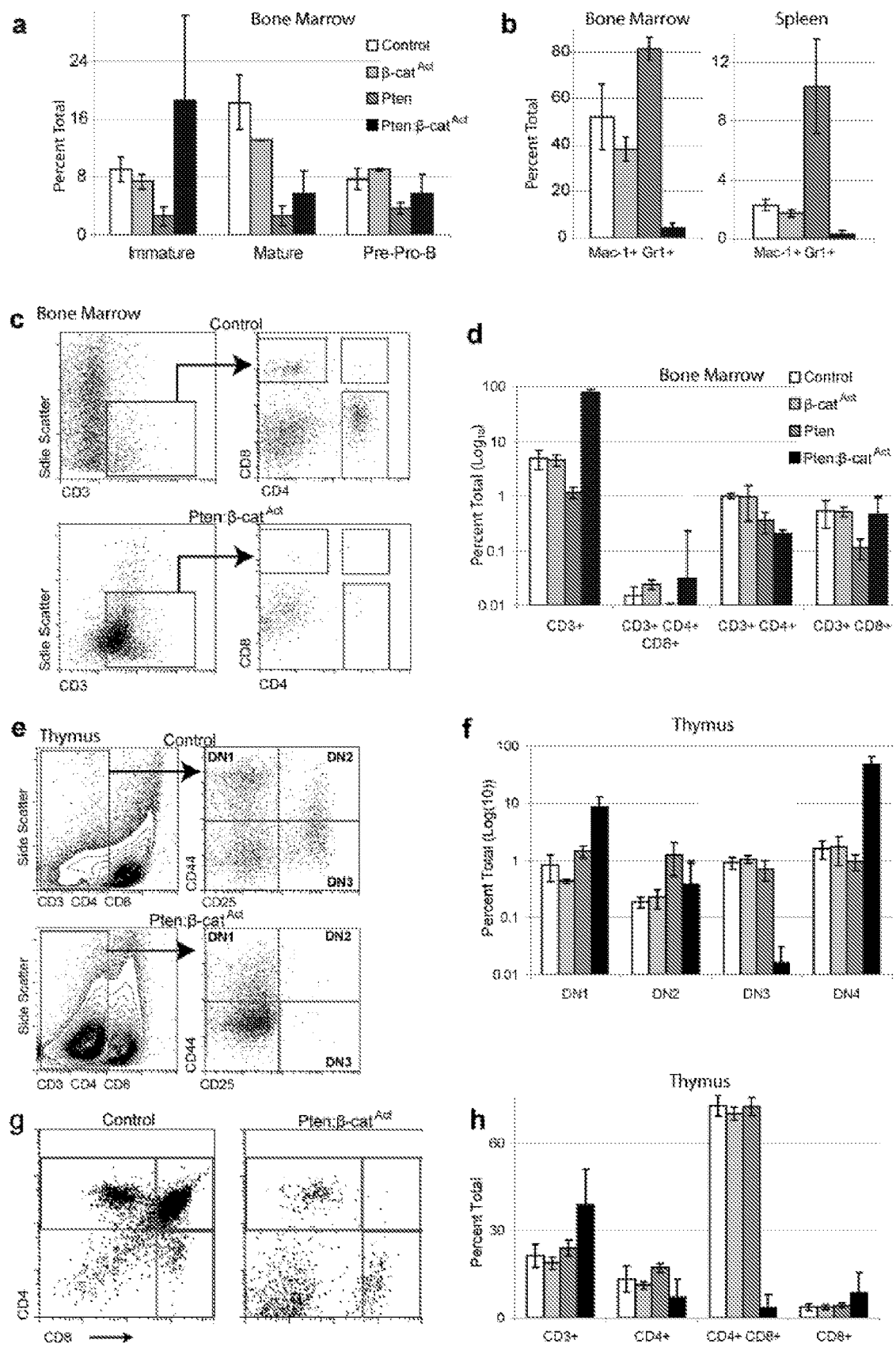
FIG. 6 illustrates hematopoietic lineage analysis in control, Pten, β-catAct, and Pten:β-catAct mice. a, Percentage of immature (B220Low, IgM+), mature (B220High, IgM+) and Pre-Pro B (B220Low, IgM−) cells in control, single and double mutant bone marrow 8-9 wpi as determined by FACS analysis. b, Percentage of Mac-1+ Gr1+ myeloid cells in bone marrow (top) and spleen (lower) in 8-9 wpi control, single and double mutants as determined by FACS analysis. c, FACS diagrams illustrating control and double mutant bone marrow analysis of T-cell lineage cells quantified in d. d, Percentage of CD3+, double and single positive T cells in control, single and double mutant bone marrow at 8-9 wpi. Note the logarithmic scale. e-f, Double Negative (DN)

Simultaneous Activation of Wnt/β-Catenin and PI3K/Akt Pathways Results in Successive Expansion of HSPCs, LSCs and T-ALL Blast Cells Previous work showed that cooperative activation of the Wnt/β-catenin and PI3K/Akt pathways drove self-renewal but resulted in leukemic transformation. The ontogeny and nature of leukemogenesis in Pten:β-cat$^{Act}$ mice that activate both pathways in HSPCs was explored. Pten:β-cat$^{Act}$ double mutants consistently and robustly developed blast crisis as indicated by >20% CD45$^{hi}$ leukemic blasts. These cells were negative for major lineage markers but expressed CD3 while being negative for CD4 and CD8, suggesting a maturation blockage in early T-cell development (FIG. 1a-b). Analysis of major lineages from BM, spleen, and thymus showed a reduction in mature lineages with a large increase in immature (double negative) thymocytes in the thymus and with CD3$^+$ blasts overtaking the BM compartment by 9-10 weeks post-induction (wpi) (FIG. 6). To trace the ontogeny of this T-cell acute lymphocytic leukemia (T-ALL), we analyzed bone marrow at earlier time points for HSPCs and LSCs, the former identified as lineage negative (Lin), Sca-1$^+$c-Kit$^+$ cells and the latter as CD3$^+$ (but otherwise Lin$^-$) and c-Kit$^{Mid}$ cells[20]. Similar to our previous study, we found a striking accumulation of HSPCs in double mutants at 6 wpi with commensurate reduction in more mature (Lin$^-$c-Kit$^+$ Sca-1$^-$) progenitor cells consistent with broad differentiation blockage (FIG. 1c; see Perry et al. 2011 for further details on HSC expansion). At this stage we also found a rare population of LSCs, which became more frequent by 8 wpi as the HSPC population collapsed (FIG. 1d). By 12 wpi, all double mutant mice succumbed to T-ALL (FIG. 1e). This rapid and consistent T-ALL development was unique to double mutants. Only 25% of Pten single mutants developed leukemia within 6 months post-induction. Histologically, the marrow cavity was largely taken over by leukemic blasts, but the trabecular bone region—the main site of the HSC niche—maintained a residual holdout of hematopoiesis (FIG. 7a). Double mutants also exhibited splenomegaly and disruption of the normal architecture (FIG. 7b-c). Interestingly, pS$^{552}$-β-catenin positive cells were particularly increased in double mutant spleens (FIG. 1f). Collectively, these data demonstrate that cooperative activation of the Wnt/β-catenin and PI3K/Akt pathways drive the progressive expansion of phenotypic HSPCs with transformation to LSCs resulting in T-ALL.

Example 2

DXR Targets pS$^{552}$-β-Catenin while Sparing Total β-Catenin

Figure 2:
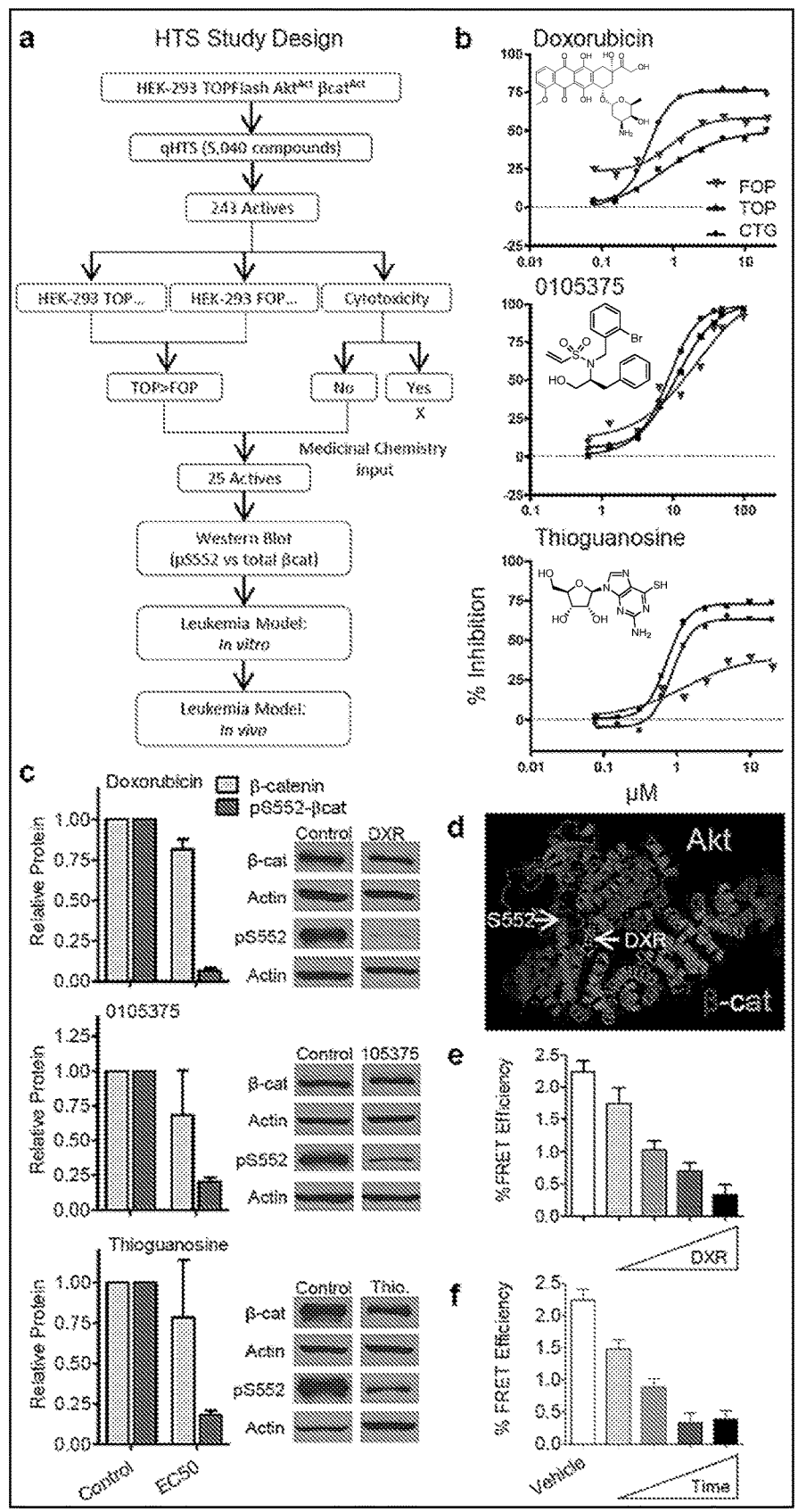
FIG. 2 shows that DXR inhibits the pSer$^{552}$ active form of β-catenin. a, Flowchart summarizing HTS design. b, Activity of compounds from validation library was tested against HEK-293 TOPFlash Akt$^{Act}$ βcat$^{Act}$ (TOP) and control HEK-293 FOPFlash Akt$^{Act}$ βcat$^{Act}$ (FOP) cells at multiple doses for inhibition of luciferase activity. Cytotoxicity profiles (CTG) of compounds were also determined. Shown are representative data from 3 compounds of interest. Dose-response data (b) were used to calculate the effective concentration of compounds resulting in 90%, 50%, and 25% inhibition of luminescence or cytotoxicity (EC$_{90}$, EC$_{50}$, and EC$_{25}$) using nonlinear regression analysis. TOP and FOP cells were treated with candidate compounds at EC$_{90}$, EC$_{50}$ and EC$_{25}$ derived from (b) for 48 hours, washed and flash frozen for Western analysis (c). See Methods for additional detail. d, Computational model showing predicted binding of Akt and DXR to β-catenin. e-f, FRET analysis verifying interaction between AKT and β-catenin. Cells transfected with EGFP-AKT and mCherry-β-catenin were treated with vehicle or 25, 50, 100, and 200 nM Doxorubicin, and FRET efficiency was determined (e). f, FRET efficiency at 0.5, 1, 2 and 3 hrs post-doxorubicin (200 nM) addition.

Since pharmacological activation of the Wnt/β-catenin and PI3K/Akt pathways in normal HSCs synergistically drives self-renewal and expansion, it was tested whether inhibition of this cooperation could prevent oncogenic self-renewal. While there was some success in reducing LSCs using a novel pan-β-catenin inhibitor, the focus was on inhibiting the pS$^{552}$-β-catenin active form of β-catenin to target the cooperative activity of the pathways more specifically and to have lower toxicity than a pan-β-catenin inhibitor (FIG. 8). High-throughput screening (HTS) identified several candidates for this specific inhibition (FIG. 2a), which was narrowed to 3 compounds based on their ability to inhibit pS$^{552}$-β-catenin with less effect on pan β-catenin: DXR, 0105375, and thioguanosine (FIG. 2b-c). Interestingly, DXR and thioguanosine are known anti-cancer agents, with DXR being among the most successful anti-cancer therapies and thioguanosine being used originally for ALL and subsequently other tumors. The novel compound 0105375 effectively inhibited pS$^{552}$-β-catenin with no significant effect on pan β-catenin, but only at relatively high concentrations (>1 µM) (FIG. 2c). Although thioguanosine inhibited pS$^{552}$-β-catenin while largely sparing pan β-catenin, it had high levels of overall toxicity (FIG. 2b-c). Most promising appeared to be DXR, which effectively inhibited pS$^{552}$-β-catenin while have only minimal effect on pan β-catenin at relatively low concentrations (FIG. 2b-c). Indeed, computational modeling indicated that both Akt and DXR bound near the pS$^{552}$ site on β-catenin (FIG. 2d).

To test whether DXR could block interaction between Akt and β-catenin, Fluorescence Resonance Energy Transfer (FRET) analysis using EGFP-AKT and mCherry-β-catenin transfected cells was performed. FRET efficiency was 2.24% in vehicle treated cells but decreased with increasing concentrations of DXR (FIG. 2e) and exposure time to DXR (FIG. 2f). However, cells transfected with EGFP only and mCherry-β-catenin showed no discernible FRET and no difference in vehicle vs. DXR treatment (FIG. 9). These data demonstrate that Akt interacts with β-catenin and that DXR effectively inhibits this interaction.

The effects of these candidate drugs on BM cells isolated from leukemic double mutants were tested in vitro. Relative to vehicle, DXR significantly reduced LSCs but not HSPCs (FIG. 10). Since thioguanosine reduced not only LSCs but also HSPCs and since 0105375 had far less potency than DXR, we focused our in vivo studies on DXR. Together, these data show that DXR can inhibit pS$^{552}$-β-catenin with minimal effects on total β-catenin. Interestingly, DXR exhibits the broadest spectrum of anti-cancer activity known and has been employed as a standard chemotherapeutic agent for decades, but severe side effects limit its use. Toxicity, however, may be reduced if DXR were repurposed as a targeted pS$^{552}$-β-catenin inhibitor rather than a DNA damaging agent.

Example 3

Low-Dose DXR Treatment Inhibits the High Level of pS552-β-Catenin Uniquely Overexpressed in Chemoresistant LSCs It was next determined whether DXR could inhibit pS$^{552}$-β-catenin in vivo. To obtain a relatively large set of leukemic mice that could be consistently used at the same stage after induction to test different treatment regimens, whole BM from uninduced Pten:β-cat$^{Act}$ mice was transplanted into irradiated recipients. This was combined at a 1:1 ratio with Cre negative BM from littermates to allow for potential competition between normal and leukemic cells and to more closely reflect clinical circumstances. After 4-6 weeks for recovery and engraftment, mice were placed on tamoxifen feed to induce recombination. After 8 weeks, leukemia was established in all recipients, which then received various treatments (FIG. 3a).

To repurpose DXR as a targeted inhibitor of pS$^{552}$-β-catenin rather than a cytotoxic chemotherapeutic drug, doses well below the typical clinical dose were used. While DXR is typically given as a bolus injection once every 3-4 weeks, $\frac{1}{40}^{th}$ the clinical equivalent dose (0.5 µg/g) was administered daily for 5 consecutive days, yielding a cumulative dose of $\frac{1}{8}^{th}$ the typical amount (termed [Low]DXR) (FIG. 3b). To determine if DXR could inhibit pS$^{552}$-β-catenin and in which cells, HSPCs, LSCs, and non-LSC blast cells were sorted from treated mice using flow cytometry and stained for pS$^{552}$-β-catenin (FIG. 3c). While pS$^{552}$-β-catenin was near background levels in blast cells and HSPCs, LSCs had an elevated average of pS$^{552}$-β-catenin. This average was reduced in LSCs isolated from mice recently treated with [Low]DXR, although consistent variability yielded no statistical significance in this difference (FIG. 3d-e).

To see how HSPCs, LSCs and blast cells responded to chemotherapy and how this might affect their pS$^{552}$-β-catenin status, additional groups were treated with chemotherapy alone (see Methods) or chemotherapy with [Low] DXR. Interestingly, LSCs, but neither HSPCs nor blast cells, consistently expressed significantly high levels of pS$^{552}$-β-catenin in response to chemotherapy. Notably, combined with [Low]DXR treatment, pS$^{552}$-β-catenin levels were significantly reduced to background levels (FIG. 3d-e). These data demonstrate first that chemotherapy induces consistently high levels of pS$^{552}$-β-catenin specifically and uniquely in LSCs, and second, that DXR can be repurposed using a low-dose to serve as an inhibitor of pS$^{552}$-β-catenin.

Example 4

Targeting pS552-β-Catenin Selectively Eliminates Chemoresistant LSCs

Next the differential effects of chemotherapy and [Low] DXR on blast cells, LSCs, and HSPCs was determined. As expected, chemotherapy substantially reduced blast cells compared to vehicle. However, it also induced a large expansion in LSCs but no significant change in HSPCs. Notably, [Low]DXR did not significantly reduce blast cells (FIG. 4a-d), but the clinical equivalent dose of DXR acted similar to chemotherapy in their reduction (FIG. 11), supporting a more specific, less cytotoxic role for [Low]DXR treatment. However, [Low]DXR significantly reduced LSCs compared to vehicle and allowed significant recovery of HSPCs. Overall, chemotherapy and [Low]DXR displayed dichotomous effects on these populations, with chemotherapy targeting blast cells but inducing LSC expansion, whereas [Low]DXR did not significantly target blasts but reduced LSCs. In combination, chemotherapy with [Low] DXR treatment not only reduced blasts and prevented LSC expansion, but also essentially eliminated detectible LSCs. Combination treatment also allowed for consistent and significant recovery of HSPCs (FIG. 4a-d).

Figure 3:
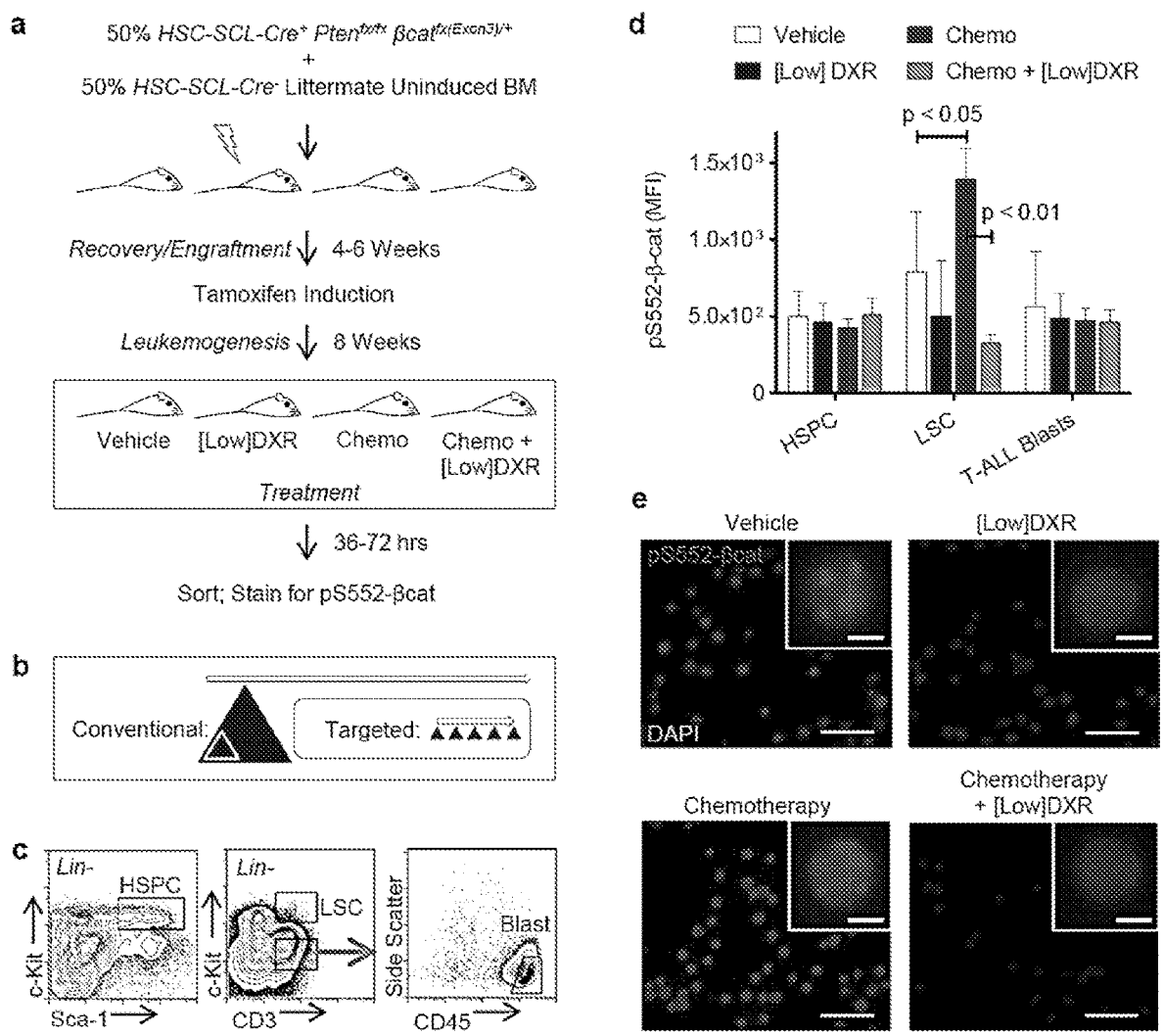
FIG. 3 shows that chemotherapy-induced high expression of pS$^{552}$-β-catenin in LSCs is inhibited by low-dose DXR treatment. a, Schematic of experimental setup for leukemia treatment mouse model system. b, Illustration of strategy for repurposing DXR as a targeted therapy. Open arrows indicate a single treatment cycle for typical clinical use of DXR and targeted use strategy (inner box) drawn to relative scales. Triangles represent DXR treatment drawn proportionally to scale. The cumulative targeted dose (distributed over 5 days consecutively) is indicated to relative scale by the inner triangle (white) (see Methods). c, Representative flow cytometry sorting gates indicating HSPC, LSC and (non-LSC) T-ALL blast cell populations. d, Populations from (c) were sorted from leukemic mice treated as indicated in (a,b) with vehicle, chemotherapy, [Low]DXR or chemotherapy+[Low]DXR and stained with Anti-pS$^{552}$-β-catenin antibody. Mean fluorescent intensity (MFI) is indicated for each population and treatment. e, Representative images of pS$^{552}$-β-catenin staining of LSCs sorted from mice treated as indicated from (d). Scale bars, 30 μm (inset 3 μm).
Figure 4:
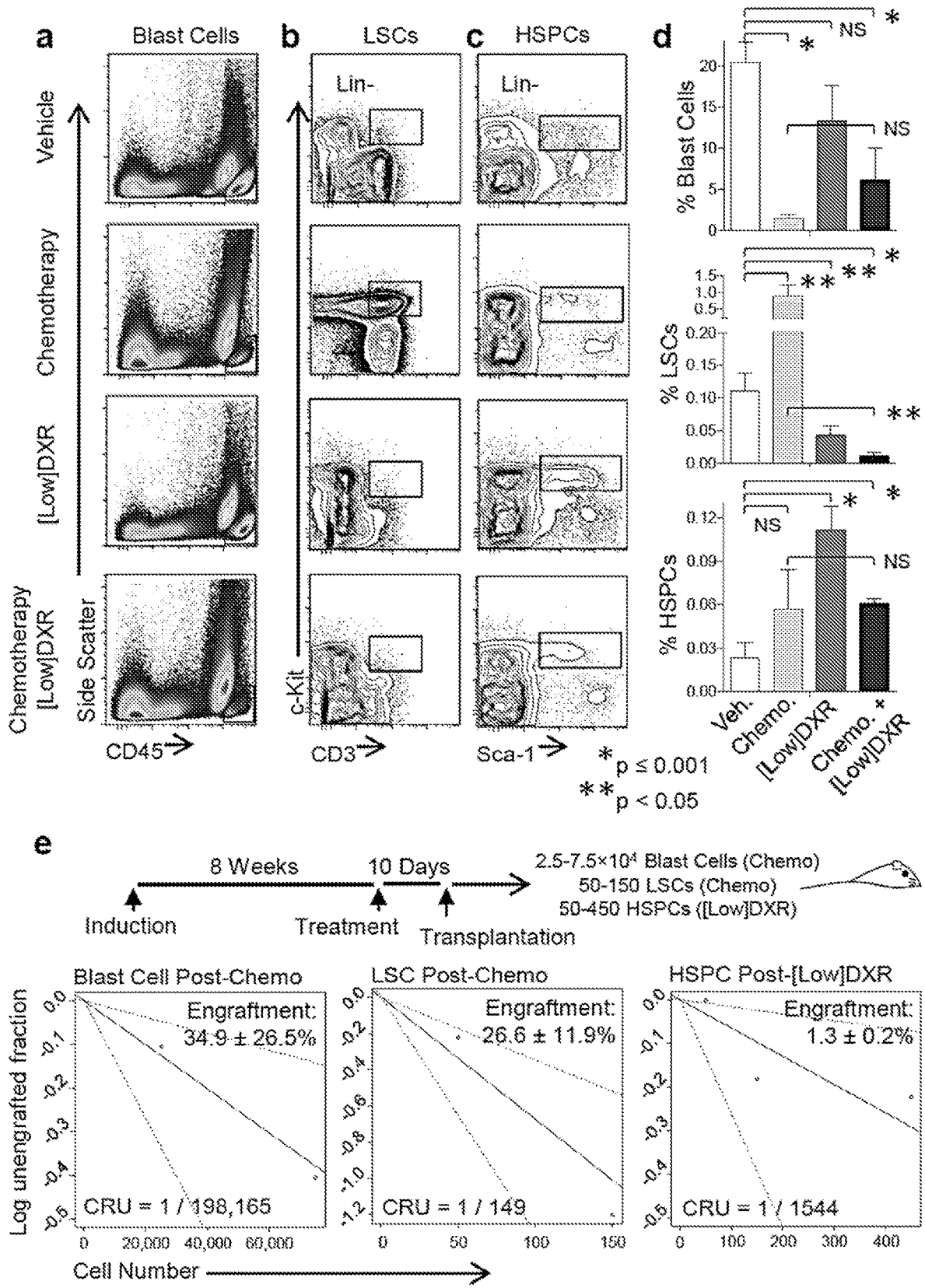
FIG. 4 shows differential response of LSCs and blast cells to chemotherapy and [Low]DXR treatment. Leukemic mice were treated with vehicle, chemotherapy, [Low]DXR or chemotherapy+[Low]DXR as described in FIG. 3a. a-c, At 10 days post-treatment, BM was analyzed by flow cytometry to determine frequency of blast cells (a), LSCs (b) and HSPCs (c). Shown are representative plots. d, Average frequency±SD of each population from a-c (n≥6 per group). e, Limiting-dilution assays to determine CRU frequency were performed on blast cells and LSCs sorted from chemotherapy treated leukemic mice and on HSPCs sorted from [Low]DXR treated mice. Engraftment 1% blast cells) was determined in NSG recipients at 10-12 weeks post-transplant.

To quantify the tumorigenic activity of LSCs relative to blast cells in chemotherapy treated mice, limiting-dilution transplants was performed into sub-lethally irradiated NOD-SKID-Il2rg$^{-/-}$ (NSG) recipients. LSCs sorted from chemotherapy treated mice exhibited a >1300-fold increase in competitive-repopulating unit (CRU) activity compared to blast cells sorted from the same donors (FIG. 4e; Table 1). LSCs sorted from chemotherapy treated mice also had a 10-fold higher CRU frequency than HSPCs sorted from [Low]DXR treated mice, and, unlike the LSCs and blast cells, these HSPCs only engrafted at low levels without developing into leukemia by 10-12 weeks post-transplant (FIG. 4e; Table 1). Together, FIGS. 3 and 4 show that chemotherapy not only fails to eliminate LSCs but also induces expression of $pS^{552}$-β-catenin and functional LSC expansion. However, [Low]DXR treatment inhibits $pS^{552}$-β-catenin expression and LSC expansion. Notably, these treatments exhibit differential effects on LSCs and blast cells.

TABLE 1

| Treatment of Donors | Transplant Population | Dose | Tested | Engrafted | Estimate | Lower | Upper |
|---|---|---|---|---|---|---|---|
| Chemo. | Blast Cells | 25,000 | 10 | 1 | 1/198,165 | 1/528,906 | 1/74,247 |
|  |  | 75,000 | 9 | 3 |  |  |  |
| Chemo. | LSCs | 50 | 10 | 2 | 1/149 | 1/289 | 1/77 |
|  |  | 150 | 10 | 7 |  |  |  |
| [Low]DXR | HSPCs | 50 | 5 | 0 | 1/1,544 | 1/6,240 | 1/383 |
|  |  | 150 | 6 | 1 |  |  |  |
|  |  | 450 | 5 | 1 |  |  |  |

Example 5

Binary Targeting of Bulk Leukemic Blasts and Chemoresistant LSCs Substantially Increases Long-Term Survival It was next determined whether LSCs are not only phenotypically but also functionally reduced by [Low]DXR treatment. A cohort of mice was established as in FIG. 3a. One week after completion of treatment with vehicle, chemotherapy, [Low]DXR, or chemotherapy+[Low]DXR, we transplanted BM from treated mice into irradiated NSG recipients to test for tumorigenic cells. Recipients treated with vehicle succumbed to leukemia in a similar manner to primary mutants following induction (FIG. 5a). However, recipients of BM from leukemic mice treated with chemotherapy succumbed more rapidly, although 25% of the group exhibited prolonged survival. The reduced survival of most recipients was consistent with LSC expansion induced by chemotherapy (FIG. 4). Nearly all (29/30) recipients of BM from mice treated with [Low]DXR alone remained healthy nearly 6 months post-transplant. Analysis of these 29 survivors revealed only trace levels of blast cells and LSCs, and HSPCs were within normal parameters (FIG. 5b). These data support the specific targeting of functional LSCs by [Low]DXR treatment.

Also most recipients of BM from chemotherapy+[Low]DXR treated mice succumbed to leukemia by 6 months post-transplant; however, their median survival was significantly extended from 44.5 days to 104.5 days compared to the chemotherapy alone group (FIG. 5a). Thus, although combination treatment essentially eliminates phenotypic LSCs, functional LSCs ultimately recover with exposure to chemotherapy. Even so, [Low]DXR treatment significantly reduces chemoresistant cells with LSC activity.

To determine long-term survival, cohorts of leukemic mice were established as in FIG. 3a but this time observed treated mice long-term without transplantation into NSG mice. While mice treated with vehicle alone succumbed to leukemia at a similar rate as untreated mice, those treated with chemotherapy alone exhibited somewhat improved overall survival; nonetheless, all still succumbed by 50 days post-treatment (FIG. 5c). [Low]DXR only treated mice exhibited only minor and insignificant improvement, likely due to the minimal and insignificant effect of [Low]DXR treatment on blast cells (FIG. 4a). However, combining chemotherapy and [Low]DXR treatment significantly increased survival compared to chemotherapy ($p<0.05$) or [Low]DXR ($p<0.01$) alone (FIG. 5c).

Although significant, these improvements were incremental in the primary treated mice (FIG. 5c). Since functional LSCs were still present following combination (chemotherapy+[Low]DXR) treatment (FIG. 5a), whiteout being bound to a particular theory, it was hypothesized that using only a single cycle of chemotherapy combined with a more sustained, maintenance treatment of [Low]DXR might better prevent LSCs from repopulating the leukemia. The potential tissue damage caused by doxorubicin, especially when giving multiple injections, makes long-term maintenance dosing of DXR impractical. DXR-loaded nanoparticles (nanoDXR) were then used not only to reduce potential tissue damage but also to allow for a slow, more sustained release of DXR during chemotherapy treatment. Because these nanoparticles provide steady, sustained release of DXR, using nanoDXR allows to alter the dosing schedule to avoid repeated, daily DXR injections. Multiple doses of free DXR and nanoDXR were tested to further optimize this treatment (FIG. 12). A $\frac{1}{8}^{th}$ clinical equivalent dose of nanoDXR delivered as a single injection on day 1 was as effective in reducing LSCs as the equivalent cumulative dose of free DXR distributed over 5 days (see Suppl. Methods). Moreover, this single injection could be reduced to a $\frac{1}{25}^{th}$ clinical equivalent with at least the same efficacy (FIG. 12). Thus, a cohort of leukemic mice was tested as before with chemotherapy combined with only a single $\frac{1}{25}^{th}$ injection of nanoDXR on day 1. Since high levels of $pS^{552}$-β-catenin were apparent only in response to chemotherapy, subsequent, weekly injections of nanoDXR were further reduced to $\frac{1}{50}^{th}$ for an additional 9 weeks of maintenance treatment. This regimen significantly reduced LSCs while also facilitating significant recovery of HSPCs compared to free [Low]DXR (FIG. 5d). Notably, median survival was extended to 139 days, with most mice succumbing only after cessation of maintenance [Low]nanoDXR (FIG. 5e). Mice surviving over 7 months post-chemotherapy treatment showed, at most, only trace levels of blast cells and LSCs with normal levels of HSPCs (FIG. 5f). Tumorigenic LSCs were tested by transplanting bone marrow from [Low]nanoDXR treated mice into NSG recipients as in FIG. 5a. Recipients showed similar survival to recipients of free [Low]DXR treated mice and even lower numbers of LSCs (FIG. 13). Together, these data show first that functional LSCs are differentially targeted by chemotherapy and [Low]DXR—with chemotherapy activating LSCs while [Low]DXR inhibits LSCs in tumorigenic assays (FIG. 5a-b). Second, that combination therapy is necessary to substantially improve survival in leukemic mice as chemotherapy eliminates blast cells while [Low]DXR reduces LSC frequency and prevents the resultant chemoresistant LSC expansion (FIG. 5c). And lastly, that chemotherapy combined with maintenance treatment using [Low]nanoDXR substantially improves long-term survival (FIG. 5e).

Discussion

Tumorigenic cells can not only resist standard chemotherapy, but also actually expand in response to it, which clarifies why anti-cancer therapy often fails. Targeting CSCs/LSCs, ideally with minimal effect on normal stem/progenitor cells, is crucial to future success. Unexpectedly, this disclosure provides that a long-used chemotherapeutic agent could be repurposed to this end. DXR acts as a topoisomerase II inhibitor at high concentrations and exhibits the broadest spectrum of anti-cancer activity known, but it's not clear why DXR would have greater efficacy in many cancers than other topoisomerase II inhibitors. However, anti-cancer drugs used as DNA damaging agents can have unanticipated effects. Topotecan, another topoisomerase II inhibitor, was found to unsilence the normally dormant paternal allele of the Ube3a gene when used at relatively low doses. Ube3a is responsible for Angelman syndrome when the maternal allele is mutated, so epigenetic de-repression of the typically normal paternal allele may alleviate this syndrome. DXR is also known to affect epigenetic states by evicting histones from open chromatin, which occurs irrespective of its ability to induce DNA breakage, and was shown to alter the transcriptome of cancer cells; however, the consequences of these effects are largely unknown. Despite using chemotherapeutic drugs for more than half a century, skilled artisans still don't fully understand their mechanism of action or why they preferentially kill cancer cells. As this current study demonstrates, understanding these effects and using drugs based on this understanding will allow for a more rational treatment of cancer. Regarding DXR, despite its success, its use is limited due to severe cardiotoxicity, necessitating a maximum life-time dosage, and other cytotoxic effects. Relapse is common in T-ALL, which carries a poor prognosis and is not improved by intensified chemotherapy. PI3K activating mutations are common in ALL, and relapsed pediatric patients often show additional activation of the Wnt pathway, frequently resulting from epigenetic changes. Thus, repurposing DXR as a targeted therapy against chemoresistant cells could avoid severe toxicity and reduce relapse. DXR nanoparticles are particularly well-suited for this effect due to their slow, sustained release and tissue distribution, which has been shown to be preferential to tumors but is markedly reduced in the heart and other vital organs (Tran, T. H. et al. Long circulating self-assembled nanoparticles from cholesterol-containing brush-like block copolymers for improved drug delivery to tumors. *Biomacromolecules* 15, 4363-4375 (2014), which is incorporated by reference herein).

Considering the critical role of Wnt/β-catenin and PI3K/Akt cooperative signaling in normal HSC self-renewal, inhibition pS$^{552}$-β-catenin was expected to have a detrimental effect on normal HSCs, and was expected to need to rescue treated mice with HSC transplantation, perhaps using established ex vivo HSC expansion system. Unexpectedly, [Low]DXR treatment allowed for and even facilitated recovery of HSPCs. Whiteout being bound to a particular theory, it's possible that, similar to the phenomenon of oncogene addiction, LSCs are 'addicted' to the β-cat/Akt mechanism of self-renewal, while HSPCs may be more flexible in using alternative pathways. Elimination of LSCs and blast cells reduces competition, allowing for subsequent recovery of HSPCs. As LSCs compete with HSPCs for niche occupancy, elimination of LSCs in particular facilitates a net recovery of HSPCs. The disclosed model system is ideal for future studies regarding this dynamic competition between LSCs and HSPCs, particularly regarding normal and tumorigenic niches in response to different treatments.

Similar gene expression signatures found in cancer stem cells and normal stem cells are predictive of clinical outcomes. Clinical evidence also shows that rare cells with self-renewal capacity often survive chemotherapeutic treatment, indicating that self-renewal may be a common, central property that, if targeted, would lead to more durable cures. The disclosure supports this potential and demonstrates a dynamic relationship between chemoresistant LSCs, bulk leukemic cells, and HSPCs. Targeting tumorigenic cells discretely from their bulk progeny and preferentially over normal stem/progenitor cells would substantially improve patient outcomes if translated to the clinic.

Example 6

Leukemic mice for the studies described here were obtained as follows. Whole bone marrow was isolated from uninduced Scl-Cre positive Pten:β-catAct mice and mixed with an equal portion of congenic, wild-type bone marrow, and transplanted into irradiated (10 Gy) Ptprc recipient mice. 4-6 weeks post-transplant, recipient mice were placed on tamoxifen feed for 2 weeks in order to induce recombination, which resulted in leukemia development by 7 weeks post-induction in all recipient mice. 7 weeks post-induction, leukemic mice were injected intravenously (via the tail vein) with 5 doses (once per day consecutively) of 0.5 mg/kg Doxorubicin ('[Low]Doxo') or given a single injection (day 1 only) of doxorubicin nanoparticles (single 0.8 mg/kg injection) ('[Low]NanoDoxo') or a single injection (day 1 only) of Doxil® (single 0.8 mg/kg injection). Chemotherapy was used concurrently (once per day for 5 consecutive days) and consisted of Nelarabine injected intravenously at 217 mg/kg and Dexamethasone (intraperitoneal injection) at 10 mg/kg. All drugs were solubilized in 45% (2-Hydroxypropyl)-β-cyclodextrin (HBC). Doxorubicin hydrochloride (Sigma; D1515) with or without Nelarabine (Selleck) was dissolved in HBC (43.4 mg/ml Nelarabine +/−0.1 mg/ml Doxorubicin) and administered IV according to the formula: Body Weight (g)×5=volume to inject (μl). Dexamethasone (BioVision) was dissolved in HBC at 2.5 mg/ml and injected IP according to the formula: Body Weight (g)×4=volume to inject (μl).

The doxorubicin nanoparticles have an average particle diameter of 138 nm. The drug loading reached as high as 22.1% (w/w). The release of Dox in PBS was steady at approximately 2% per day, with 24% released in 12 days. The nanoparticles significantly increased the circulation time of the drug in blood compared to free Dox. Pharmacokinetics and biodistribution of nanoparticle-based Dox in mice bearing subcutaneous tumors showed higher blood concentrations and lower accumulation in heart, lung, kidney, spleen and liver compared with free Dox at 24 h after intravenous injection, indicating a much greater safety profile (FIG. 15a-b). Cardiotoxicity was tested based on cardiac troponin I level and histology. No heart damage was identified after treating with doxorubicin nanoparticles (5 mg/kg once per week) for 2 months, while free Dox at 1 mg/kg (8 doses) and high single dose showed cardiotoxicity (FIG. 15-c).

FIG. 14 shows that doxorubicin nanoparticles have enhanced effectiveness in eliminating leukemic stem cells and facilitating normal hematopoietic stem/progenitor cell recovery compared to Doxil®. While cytotoxic chemotherapy induces LSC expansion, low-dose doxorubicin administered daily for five days prevents this expansion and even facilitates recovery of HSPCs. Doxorubicin nanoparticles allow for further reduce LSCs compared to free doxorubicin and effectively eliminate this population. This effect is obtained through only a single low-dose injection on day 1. Doxil® is not as effective at preventing the LSC expansion induced by chemotherapy or at facilitating HSPC recovery as Doxorubicin Nanoparticles.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method of treating leukemia, comprising administering to a subject that has leukemia resistant to radiation therapy, chemotherapy, immunotherapy, or any combination thereof a pharmaceutically active molecule that is capable of selectively inhibiting one or more of p-$S^{552}$-β-catenin, p-$T^{217}$-β-catenin, p-$T^{332}$-β-catenin, or p-$S^{675}$-β-catenin production or activity, wherein the pharmaceutically active molecule is administered in an amount effective to reduce or limit leukemia-initiating cells, wherein the pharmaceutically active molecule is administered in one or more nanoparticle compositions comprising a block copolymer in a core/shell form, wherein the block copolymer comprises:

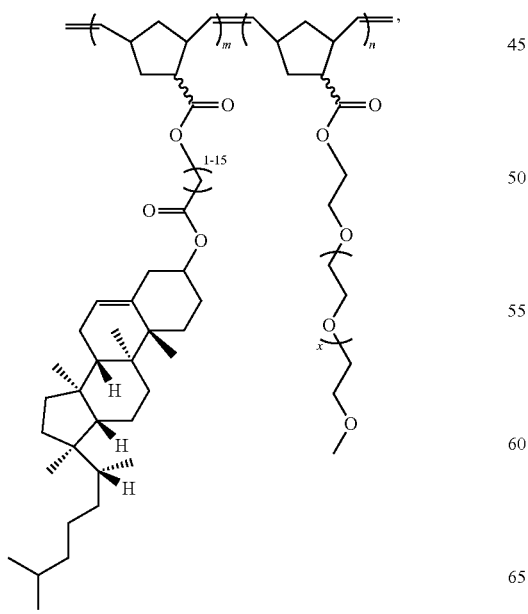

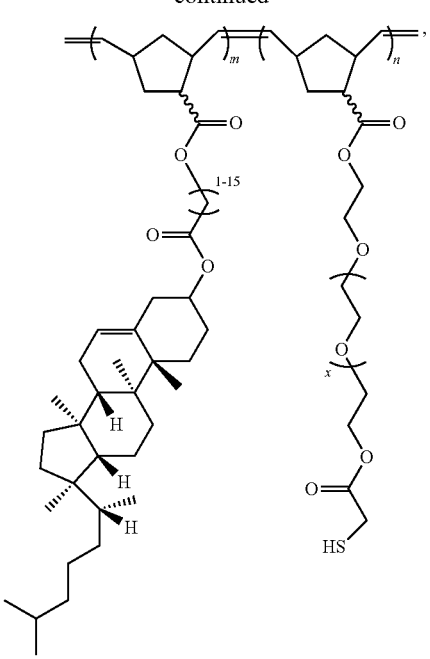

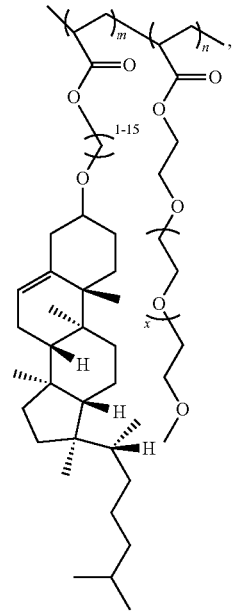

-continued

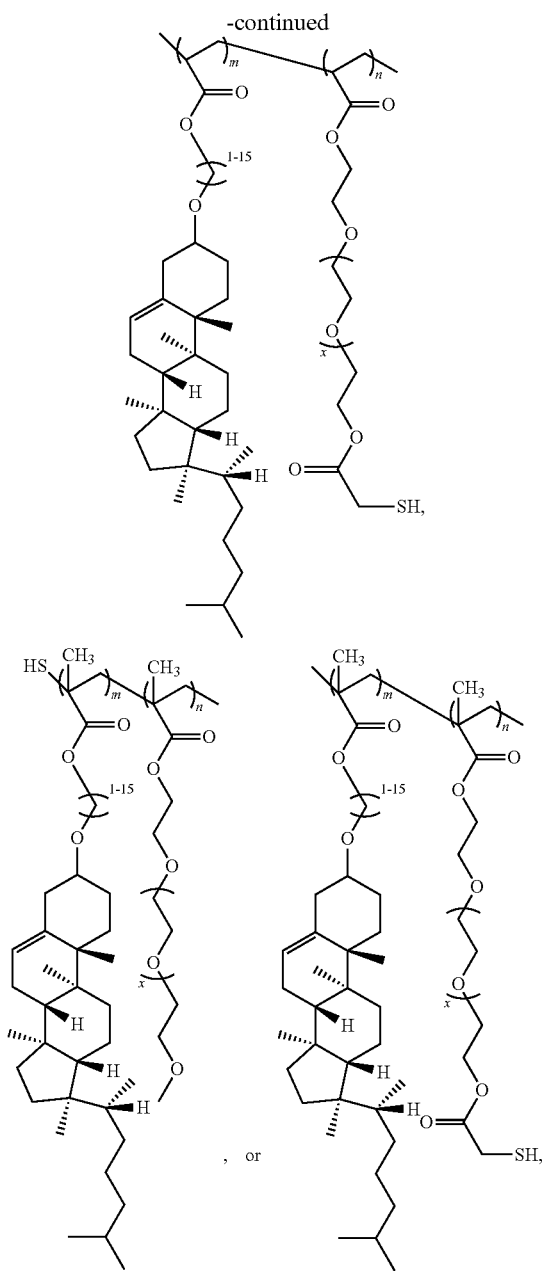

, or wherein
x is an integer between about 3 and about 100;
m is an integer between about 5 and about 200; and
n is an integer between about 5 and about 100.

2. The method of claim 1, wherein the pharmaceutically active molecule is administered in a low dose.

3. The method of claim 2, wherein the subject is a human subject, and the low dose is about ⅕ to ½₀ of a human clinical dose of the pharmaceutically active molecule when dosed for chemotherapy.

4. The method of claim 1, wherein the pharmaceutically active molecule is administered in a nanoparticle formulation.

5. The method of claim 1, wherein the pharmaceutically active molecule is anthracycline, doxorubicin, daunorubicin, or a pharmaceutically acceptable salt thereof.

6. The method of claim 1, wherein the pharmaceutically active molecule is doxorubicin, or a pharmaceutically acceptable salt thereof.

7. The method of claim 6, wherein the doxorubicin is administered in a dose of up to about 10 mg/m² per day.

8. The method of claim 1, comprising administering a combination of two different nanoparticle compositions.

9. The method of claim 8, wherein a first nanoparticle composition comprises pharmaceutically active molecule that is-doxorubicin.

10. The method of claim 9, wherein a second nanoparticle composition comprises pharmaceutically active molecule selected from the group consisting of daunorubicin, vincristine, epirubicin, idarubicin, valrubicin, mitoxantrone, paclitaxel, docetaxel, cisplatin, camptothecin, irinotecan, 5-fluorouracil, methotrexate, and dexamethasone.

11. The method of claim 1, wherein the nanoparticle composition further comprises one or more metal nanoparticles or quantum dots.

12. A method of treating leukemia, comprising administering to a human subject in need thereof a pharmaceutically active molecule that is capable of selectively inhibiting one or more of p-S$^{552}$-β-catenin, p-T$^{217}$-β-catenin, p-T$^{332}$-β-catenin, or p-S$^{675}$-β-catenin production or activity, wherein the pharmaceutically active molecule is administered in an amount of about ⅕ to ½₀ of a human clinical dose of the pharmaceutically active molecule when dosed for chemotherapy, the amount effective to reduce or limit leukemia-initiating cells, wherein the pharmaceutically active molecule is administered in one or more nanoparticle compositions comprising a block copolymer in a core/shell form, wherein the block copolymer comprises:

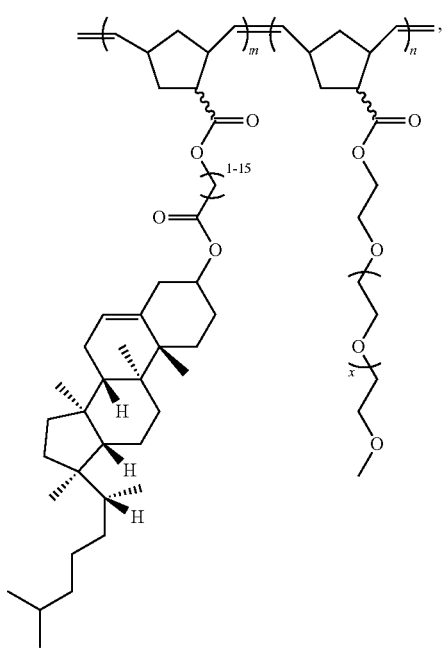

33
-continued
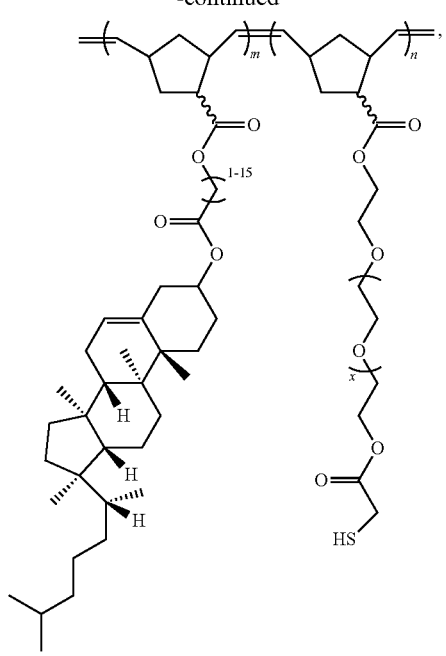
34
-continued
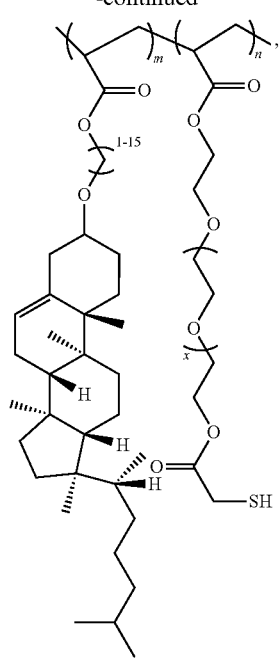
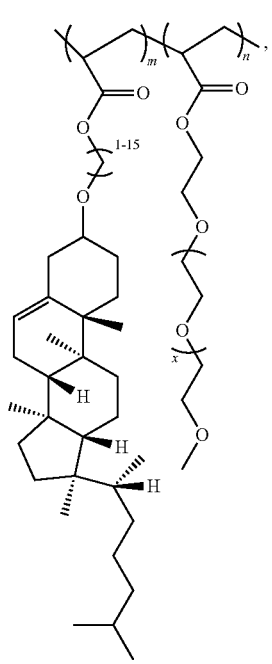
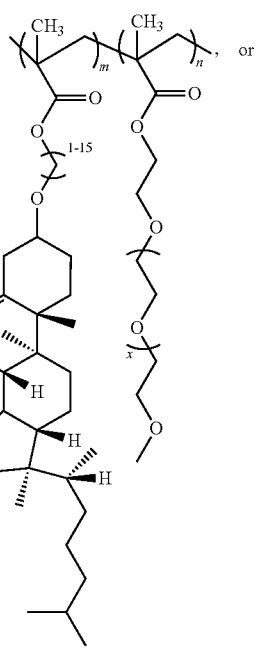, or -continued
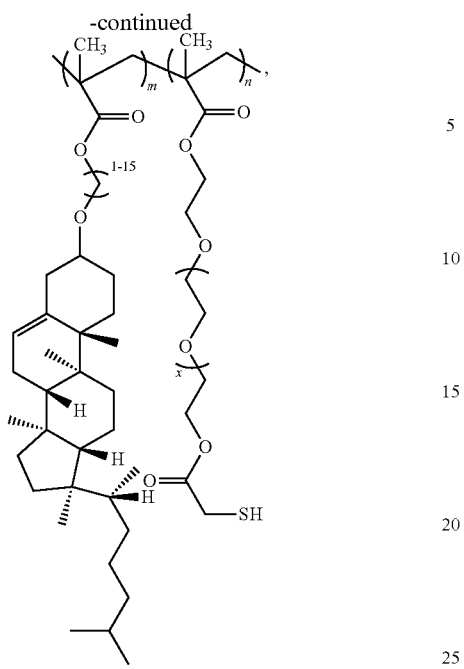
wherein
x is an integer between about 3 and about 100;
m is an integer between about 5 and about 200; and
n is an integer between about 5 and about 100.
* * * * *